United States Patent
Timmins et al.

(10) Patent No.: US 9,579,381 B2
(45) Date of Patent: Feb. 28, 2017

(54) MAGNETODYNAMIC ACTIVATION OF $^{13}$C-ACYL ISONIAZID AND ISONIAZID AND ETHIONAMIDE DERIVATIVES

(71) Applicant: STC.UNM, Albuquerque, NM (US)

(72) Inventors: Graham Timmins, Albuquerque, NM (US); Seong Won Choi, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 0 days.

(21) Appl. No.: 14/426,543

(22) PCT Filed: Sep. 6, 2013

(86) PCT No.: PCT/US2013/058521
§ 371 (c)(1),
(2) Date: Mar. 6, 2015

(87) PCT Pub. No.: WO2014/039829
PCT Pub. Date: Mar. 13, 2014

(65) Prior Publication Data
US 2015/0246126 A1 Sep. 3, 2015

Related U.S. Application Data

(60) Provisional application No. 61/698,070, filed on Sep. 7, 2012.

(51) Int. Cl.
*A61K 31/4409* (2006.01)
*A61K 41/00* (2006.01)

(52) U.S. Cl.
CPC ...... *A61K 41/0052* (2013.01); *A61K 31/4409* (2013.01)

(58) Field of Classification Search
CPC .................. A61K 31/4409; A61K 41/0052
See application file for complete search history.

(56) References Cited

U.S. PATENT DOCUMENTS

2011/0218220 A1 * 9/2011 Timmins ............. A61K 9/0019
514/354

FOREIGN PATENT DOCUMENTS

WO    WO 2009025820 A2 *  2/2009  .......... A61K 9/0019

OTHER PUBLICATIONS

Elssner et al.; "Isolation, Identification, and Synthesis of γ-Butyrobetainyl-CoA and Crotonobetainyl-CoA, Compounds Involved in Carnitine metabolism of *E. coli*"; 2000; Biochemistry; 39: 10761-10769.*

* cited by examiner

*Primary Examiner* — Timothy Thomas
(74) *Attorney, Agent, or Firm* — Henry D. Coleman; R. Neil Sudol

(57) ABSTRACT

The invention provides method of treating a subject suffering from, or at risk of developing, a *Mycobacterium* infection by administering to the subject a therapeutically-effective amount of isotopically labeled isoniazid and/or ethionamide, or an analog, derivative or prodrug thereof, and exposing the subject to a magnetic field.

25 Claims, 16 Drawing Sheets

Figure 1:
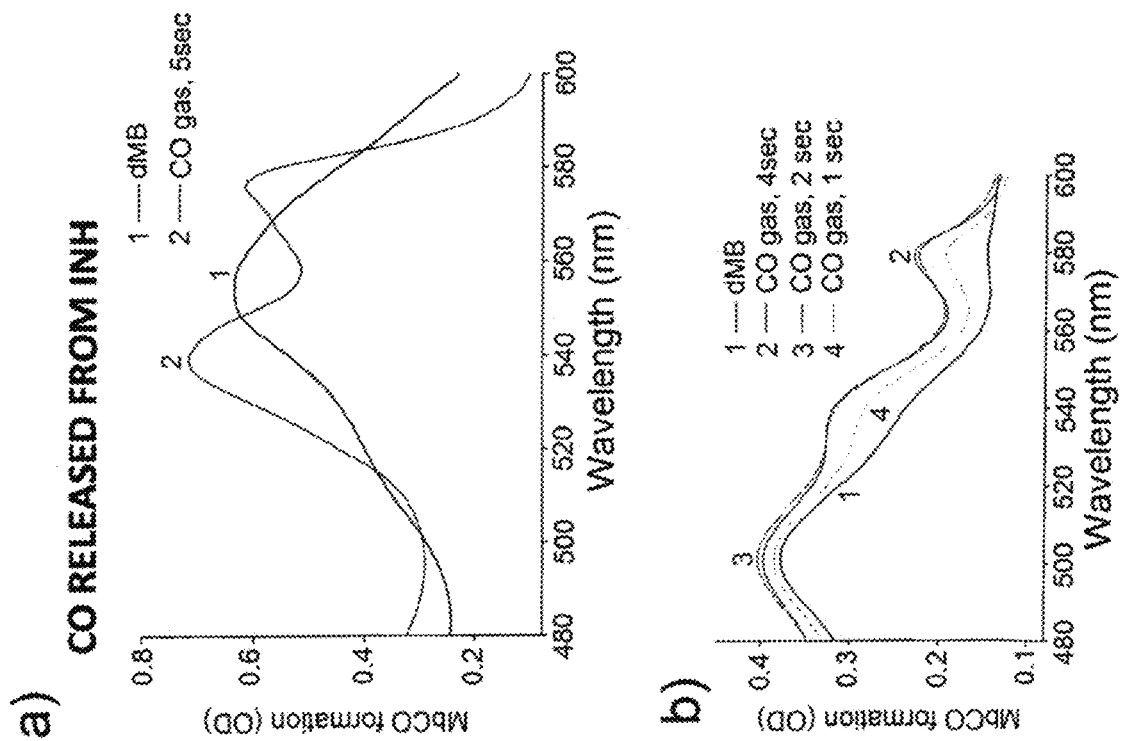

CO release from INH proportional to INH or KatG

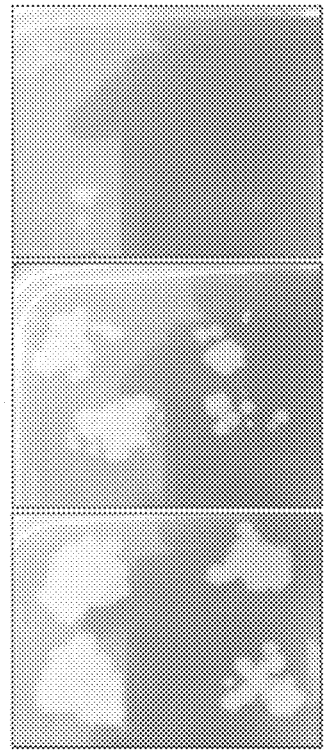
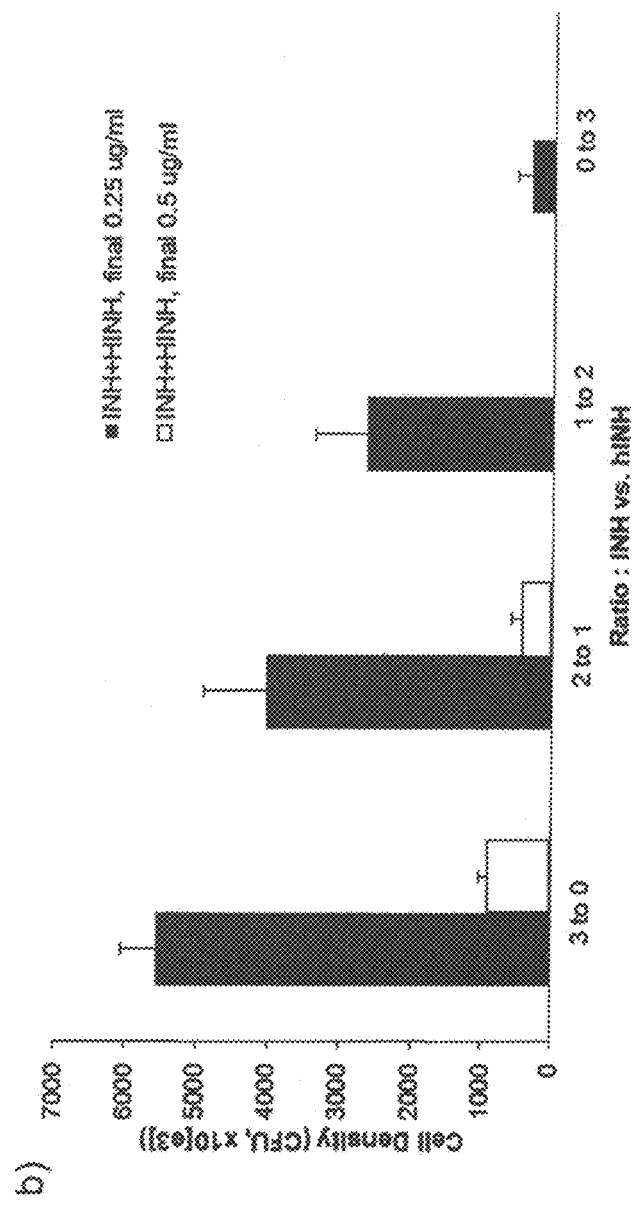
FIGURE 6

MAGNETODYNAMIC ACTIVATION OF 13 C-ACYL ISONIAZID AND ISONIAZID AND ETHIONAMIDE DERIVATIVES

RELATED APPLICATIONS AND GOVERNMENT SUPPORT

This application is a United States national phase patent application based upon international Patent Application No. PCT/US2013/058521 filed Sep. 6, 2013, entitled "Magnetodynamic Activation of 13C-acyl Isoniazid and Isoniaizid and Ethionamide Derivatives", said application claiming the benefit of priority of U.S. Provisional Application Ser. No. 61/698,070, filed Sep. 7, 2012, and entitled "Magnetodynamic Activation of $^{13}$C-acyl Isoniazid", the entire contents of which applications are hereby incorporated by reference.

FIELD OF THE INVENTION

The present invention is directed to the unexpected discovery that the antitubercular activity of $^{13}$C-acyl isoniazid (hINH) and related compounds as disclosed herein is increased substantially by the combined use of the drug, and a static magnetic field (e.g., about 50-300 gauss, 5-300 mT, preferably about 140 gauss, 0.14 mT). Combined use of magnetic field and hINH gave a substantially better in vitro killing than just hINH alone in *M tuberculosis* and an isoniazid resistant strain (KatG S315T mutant). Combined hINH and static magnetic field may find clinical use in tuberculosis (including drug resistant such as isoniazid resistant and multiple drug resistant tuberculosis) treatment in many ways, including through decreasing treatment times in isoniazid sensitive TB (more rapid recovery/cure), or in allowing treatment of drug resistant (e.g. isoniazid or ethionamide resistant) strains and/or multiple resistant strains of tuberculosis.

BACKGROUND OF THE INVENTION

Isoniazid (INH) is a pro-drug that is activated by catalase peroxidase (KatG) of *Mycobacterium tuberculosis* (Mtb) to produce isonicotinyol (INacyl) radicals that react with NAD to produce mycolate synthesis inhibitors.

Recently, it has been shown that isoniazid specifically substituted in the acyl position with $^{13}$C greatly increase isoniazid activity, through enhanced formation of INH-NAD and NADP adducts after its activation by the bacterial enzyme KatG, with these adducts being the species that are highly toxic to mycobacteria. It is believed that this is due to isotope effects on several steps of the pathway, although effects in the reversibility of acyl radical addition to the NAD, perhaps play the major role. It has been shown that another major TB drug, ethionamide (and its related compound prothionamide), undergoes almost identical activation and adduct formation chemistries (Wang, et al. *J. Exp. Med.* 204; 73-8 (2007)).

We found that INacyl radicals also decompose to release CO, and so lose the ability to produce INacyl-NAD adducts. Since CO induces dormancy in Mtb, we hypothesized that reducing this decarbonylation by selective $^{13}$C substitution (to produce heavy isoniazid, hINH) would increase activity of the resultant drug by maximizing INacyl-NAD formation, and minimizing dormancy induction by CO. Here, we describe how this $^{13}$C magnetic isotope effect (MIE) can produce more effective drugs in combination with static magnetic fields greater than the Earth magnetic field.

SUMMARY OF THE INVENTION

In one embodiment, the invention provides a method of treating a subject suffering from, or at risk of developing, a *Mycobacterium* infection by:

(a) administering to the subject a therapeutically-effective amount of isotopically labeled isoniazid and/or ethionamide, or an analog, derivative or prodrug thereof; and (b) exposing the subject to a magnetic field.

In a preferred embodiment, the exposure of the subject to the magnetic field occurs concurrently with the administration of the therapeutically-effective amount of isotopically labeled isoniazid and/or ethionamide, or an analog, derivative or prodrug thereof.

The magnetic field which can be used in the methods of treatment of the invention ranges from about 10 to about 1,000 Gauss, more often about 50-250 Gauss, even more often about 100-200 Gauss, still more often about 140-160 Gauss, and most often has a value of around 150 Gauss. FIG. 5 illustrates the magnetic field strength effect. It is believed that the magnetic field effect begins at around 50 gauss, reaches a maximize value at around 140 G, and begins to taper in the range of about 600-1,000 G.

The enhanced therapeutic magnetic field effect described herein is maximized when the active ingredient preferably is:

(a) an isoniazid compound whose acyl group contains $^{13}$C and/or $^{17}$O, e.g.:

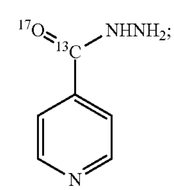

or (b) an ethionamide compound whose thioamide group contains $^{13}$C and/or $^{33}$S, e.g.:

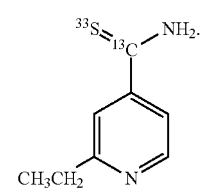

Such compounds are described further hereinafter and are used in preferred methods of treatment of the invention. Enhanced therapeutic magnetic field effects can also be achieved by using the various other isotopes described herein.

In certain aspects, methods of treatment of the invention use compounds according to the chemical structure:

where X is an oxygen or a sulfur atom selected from the group consisting of $^{16}O$, $^{17}O$, $^{18}O$, $^{32}S$, $^{33}S$ and $^{34}S$; (preferably $^{17}O$ and/or $^{33}S$);
Y is a carbon atom selected from the group consisting of $^{12}C$ and $^{13}C$ (preferably $^{13}C$);
Z is a $NH_2$ group or a $NHNH_2$ group, which group is optionally isotopically labeled with at least one $^{15}N$ atom, preferably two $^{15}N$ atoms in the case of a $NHNH_2$ group;
R is H or a $C_1$-$C_3$ alkyl group, preferably H or an ethyl group, with the proviso that R is H and Z is an optionally isotopically labeled $NHNH_2$ group when X is an oxygen atom and R is a $C_1$-$C_3$ alkyl group, preferably an ethyl group and Z is an optionally isotopically labeled $NH_2$ group when X is a sulfur atom;
wherein at least one of X, Y and Z is isotopically labeled, or a pharmaceutically acceptable salt thereof.

In certain aspects, methods of treatment of the invention use compounds according to the chemical structure:

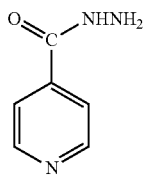

or a pharmaceutically acceptable salt thereof wherein the compound contains at least one isotopically labeled atom, preferably carbon-13, nitrogen-15 or oxygen-17 or oxygen-18 in the exocyclic acyl hydrazide moiety. It is noted that preferred compounds according to the present invention are labeled at positions where the labeled atom participates in a reaction to produce adduct formation in *Mycobacterium*.

In certain aspects, methods of treatment of the invention use the following specific isotopically labeled compounds of isoniazid:

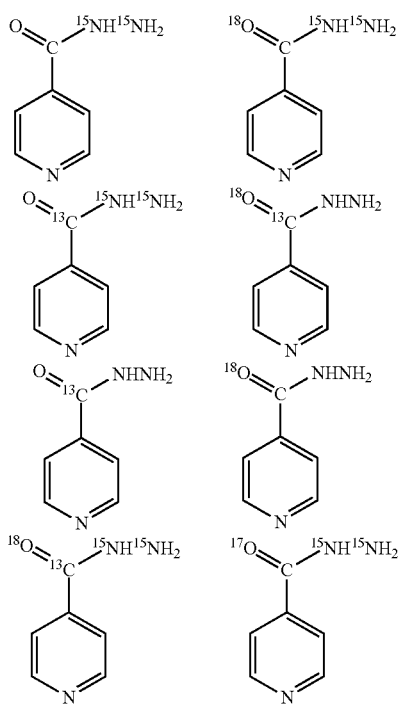

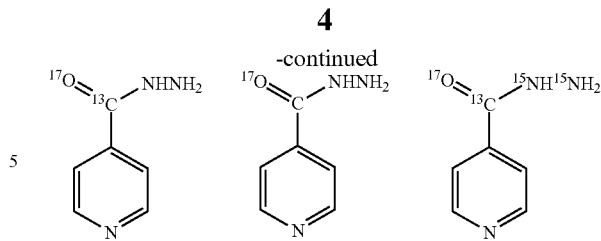

In other aspects, methods of treatment of the invention use compounds according to the chemical structure:

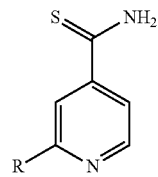

where R is a $C_1$-$C_3$ alkyl group, preferably a $C_2$-$C_3$ alkyl group (ethionamide, propionamide), more preferably an ethyl group (ethionamide) or a pharmaceutically acceptable salt thereof wherein the compound contains at least one isotopically labeled atom, preferably carbon-13, nitrogen-15, sulfur-33 or sulfur-34 at the exocyclic thioamide position. It is noted that preferred compounds according to the present invention are labeled at positions where the labeled atom participates in a reaction to produce adduct formation in *Mycobacterium*. Compounds based upon ethionamide which are isotopically labeled with carbon-13, sulfur-33, sulfur-34 or nitrogen-15, which are preferably placed in the thionamide moiety of the compounds of interest.

In certain aspects, methods of treatment of the invention use the following specific isotopically labeled compounds of ethionamide:

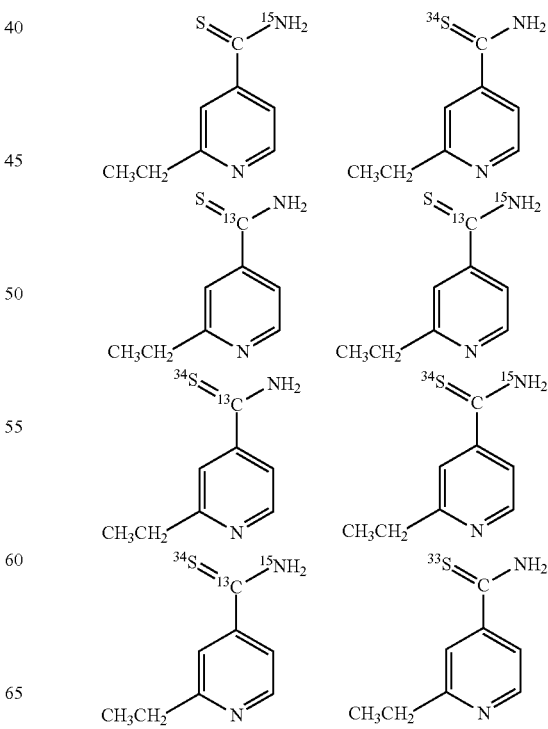

-continued

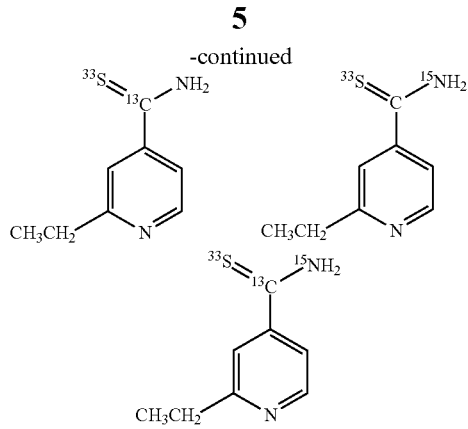

The methods of treatment described herein represent the first example of using a known therapeutic approach ($^{13}C$ magnetic isotope effect (MIE)) that is further enhanced by application of an external magnetic field to enhance the efficacy of isoniazid and/or ethionamide, or an analog, derivative or prodrug thereof, in treating a *Mycobacterium* infection (e.g. a tuberculosis infection), even an infection that would otherwise be resistant to therapy using INH alone.

By achieving higher levels of hNIH activity with reduced drug-induced dormancy, methods of treatment of the invention enable more rapid and effective treatment than INH-containing drug regimens.

These and other aspects of the invention are described in detail in the Detailed Description of the Invention.

BRIEF DESCRIPTION OF THE FIGURES

FIG. 1 shows that (FIG. 1*a*, FIG. 1*b*) MbCO was formed by CO released from INH. (FIG. 1*c*) deoxyMb- containing $Na_2S04$ (A, 0.004%; B, 0.1%) was flushed with CO gas as indicated and analyzed to show CO release in the presence or absence of INH.

FIG. 2 shows that CO release was dependent on (FIG. 2*a*) INH or (FIG. 2*b*) KatG amount. Various amounts of (FIG. 2*a*) INH or (FIG. 2*b*) KatG were mixed with 1 mM tBHP and KatG at 0.448 μg/μl in 10 mM phosphate buffer, pH 7, 50 μl on ice.

FIG. 3, shows that $NAD^+$ or hINH inhibited formation of MbCO. Various dosages of (FIG. 3*a*) NAD+ or (FIG. 3*b*) hINH were incubated with Kat G at 22.44 μg per reaction, and 1 mM tBHP in 10 mM phosphate buffer, pH7.

FIG. 4, shows that CO released form INH or hINH was detected by isotope radio mass spectrometry. 50 μg of (FIG. 4*a*) INH or (FIG. 4*b*) hINH was incubated with 540 μM MnPP in 0.5 ml and the results presented. (FIG. 4*c*) shows the concentration of d13C in CO for INH or hINH.

FIG. 5, shows real time PCR measurement of RNA (transcript) levels of dormancy genes in *M. bovis*. (FIG. 5*a*) BCG or (FIG. 5*b*) Mtb H37Rv treated with INH or hINH for 4 hours as shown.

FIG. 6, shows that (FIG. 6*a*) Mtb BCG culture was treated with INH and hINH at the indicated dose. (FIG. 6*b*) hINH is tuberculocidal dose-dependent against *M. bovis* BCG.

FIG. 7A shows that (FIG. 7Aa) Mtb H37Rv or (FIG. 7Ab) S315T culture was treated with INH or hINH at the indicated dosage.

FIG. 8 shows (FIG. 8*a*) the arrangement of tubes in the magnet and (FIG. 8*b*, FIG. 8*c*) that the tuberculocidal activity of hINH was further enhanced by a magnetic field.

FIG. 8A shows *M. bovis* BCG, (FIG. 8Aa) Mtb H37Rv and (FIG. 8Ab) S315T (an INH resistant strain) were treated with INH or hINH, placed under magnetic field at 14 mT (140 gauss) for 4 hours (BCG) or 5 days (Rv).

FIG. 9 shows that hINH is more tuberculocidal than INH. Mice (groups of 5) were aerosol infected with Mtb H37Rv and treated daily by gavage (5 days/week) with INH or hINH.

FIG. 10 shows (FIG. 10*a*) the S315T culture treated with INH or hINH at the indicated dosage and that (FIG. 10*b*) the tuberculocidal activity of hINH was further enhanced by external magnet.

FIG. 10A shows the tuberculocidal activity of hINH on the H37Rv culture was further enhanced by the external magnet after (FIG. 10Aa) 4 hours and (FIG. 10Ab) 5 days.

FIG. 10B shows the tuberculocidal activity of hINH on the S215T culture was further enhanced by the external magnet after (FIG. 10Ba) 4 hours and (FIG. 10Bb) 5 days.

FIG. 11. Effect of magnetic field on hINH. Mtb H37Rv was treated with hINH at 0.05 μg/ml and placed under various magnetic fields for 5 days.

DETAILED DESCRIPTION OF THE INVENTION

The following terms shall be used to describe the present invention. In instances where a term is not specifically defined herein, the term shall be accorded its meaning, within context, as understood by those of ordinary skill in the art.

The term "compound" shall mean any specific compound which is disclosed within this specification and typically means an isotopically labeled compound. Pharmaceutically acceptable salts (generally, pyridinium salts) are also compounds for use in the present invention. The term compound, as it relates to the present invention, also refers to isotopically labeled isoniazid, as well as compounds/derivatives of ethionamide, such as propionamide. +

The term "effective" when used in context, shall mean any amount of a compound or component which is used to produce an intended result within the context of its use. In the case of compounds according to the present invention, the term effective generally refers to a therapeutically effective amount of compound which will inhibit the growth (bacteriastatic) and/or produce a die-off (bacteriocidal) of *Mycobacterium*. This term is distinguishable from a diagnostic effective amount of isoniazid and/or ethionamide which may be used short term (for example, a few hours) to diagnose the presence of a tuberculosis infection in a patient at risk. Agents useful in treating tuberculosis infections are treated with an amount and for a duration effective in treating (i.e., in eliminating or at least stabilizing) the tuberculosis infection in the patient.

In the present invention, isotopically labeled isoniazid, ethionamide and/or propionamide (preferably, isoniazid) administered to a patient exposed to a magnetic field is often combined in therapeutically effective amounts with at least one and preferably more than one additional anti-tuberculosis agent selected from the group consisting of aminosalicyclic acid/aminosalicylate sodium, capreomycin sulfate, clofazimine, cycloserine, ethambutol hydrochloride, kanamycin sulfate, pyrazinamide, rifabutin, rifampin, rifapentine, streptomycin sulfate and mixtures thereof, all in therapeutically effective amounts, Therapeutically effective amounts of these agents generally range from as little as 1 mg/kg per day up to 50 mg/kg per day (100 mg up to several mg per day). Isoniazid and ethionamide are usually administered to a patient in therapeutically effective amounts ranging from about 5 mg/kg per day to about 20 mg/kg per day up to about 300-500 mg. In certain aspects therapeutic compounds may be administered daily, several times a week (e.g. 5 times a week) or once or twice weekly. Therapy generally continues for at least several weeks to 2 months and up to a year or more depending upon the severity of the infection and the response of the patient to therapeutic intervention.

A typical oral dose of isoniazid and/or ethionamide is at least about 25 mg and is preferably at least about 50 mg. An oral dosage form of at least 75 mg of isoniazid or ethionamide or 100 mg may be given up to 3 to 4 times daily (QID).

In certain preferred aspects, therapy may have a minimum duration of 6 months (26 weeks), and consist of an initial intensive phase (2 months) and a continuation phase (usually either 4 or 7 months).

Isotopically labeled isoniazid and/or ethionamide may be combined with effective amounts of pyridoxine (Hexabetalin), 10-50 mg/kg per day or more, in order to reduce the side effects of isoniazid/ethionamide therapy.

In a preferred method of treating previously untreated patients infected with tuberculosis, a combination of isoniazid-rifampin-pyrazinamide-ethambutol is utilized in therapeutically effective amounts to treat the patient. In this aspect of the invention, isoniazid is generally used at a concentration of about 5-10 mg/kg per day up to about 300 mg (or more, depending of the weight of the patient) per day. Rifampin is used at a concentration ranging from about 10 to 20 mg/kg per day up to about 600 mg per day. Pyrazinamide is used at a concentration ranging from 15 to 30 mg/kg per day up to about 2 grams. Ethambutol is used at a concentration ranging from about 10 to 25 mg/kg per day up to about 1 gram.

In other embodiments, a combination of ethionamide and gatifloxacin in therapeutically effective amounts with or without pyrazinamide may be used to treat tuberculosis. In this aspect of the invention, ethionamide in therapeutically effective amounts (about 5-25 mg/kg per day) and gatifloxacin (15-100 mg/kg per day) are used in amounts generally ranging from about several hundred mg per day or more up to several grams per day.

The following table represents a series of recommended therapeutic approaches to tuberculsosis therapy. All of the therapies indicated in Table 1A include the use of isoniazid. The present isotopically labeled isoniazid compound may be substituted for indicated isoniazid. These are recommended therapies. The approach to tuberculosis therapy may be varied to provide effective approaches. Ethionamide may be substituted for isoniazid at slightly higher dosages. It is noted that in each of the therapies described hereinbelow, either at administration of the isotopically labeled isoniazid or other active compound, or at administration or during periods of therapy, a magnetic field as otherwise described herein is applied to the patient undergoing therapy to enhance delivery of the active agent to the site of infection in a target tissue.

TABLE 1A

Recommended Regimens[1a] for Culture-Positive, Drug-Susceptible Pulmonary Tuberculosis

| Initial Phase | Continuation Phase | Drugs[1b] | Dosing Interval and Doses[1c] (minimum duration) | Total Doses for Both Phases (total minimum duration) |
|---|---|---|---|---|
| Regimen 1 | | INH-RIF-PZA-EMB | 7 days/wk for 56 doses (8 wks) OR 5 days/wk for 40 doses (8 wks) | |
| | 1a | INH-RIF | 7 days/wk for 126 doses (18 wks) OR 5 days/wk for 90 doses (18 wks)[1d] | 7 days/wk = 182 doses OR 5 days/wk = 130 doses (total 26 wks) |
| | 1b | INH-RIF | twice weekly for 36 doses (18 wks)[1d 1e] | 7 days/wk initially = 92 doses OR 5 days/wk initially = 76 doses (total 26 wks) |
| | 1c[1f] | INH-RPT | once weekly for 18 doses (18 wks)[1d] | 7 days/wk initially = 74 doses OR 5 days/wk initially = 58 doses (total 26 wks) |
| Regimen 2 | | INH-RIF-PZA-EMB | 7 days/wk for 14 doses (2 wks) then twice weekly for 12 doses (6 wks) OR 5 days/wk for 10 doses (2 wks) then twice weekly for 12 doses (6 wks) | |
| | 2a | INH-RIF | twice weekly for 36 doses (18 wks)[1d 1e] | 7 days/wk initially = 62 doses OR 5 days/wk initially = 58 doses (total 26 wks) |
| | 2b[1f] | INH-RPT | once weekly for 18 doses (18 wks)[1d] | 7 days/wk initially = 44 doses OR 5 days/wk initially = 40 doses (total 26 wks) |
| Regimen 3 | | INH-RIF-PZA-EMB | 3 times weekly for 24 doses (8 wks) | |
| | 3a | INH-RIF | 3 times weekly for 54 doses (18 wks)[1d] | 78 doses (total 26 wks) |
| Regimen 4 | | INH-RIF-EMB | 7 days/wk for 56 doses (8 wks) OR 5 days/wk for 40 doses (8 wks) | |

TABLE 1A-continued

Recommended Regimens[1a] for Culture-Positive, Drug-Susceptible Pulmonary Tuberculosis

| Initial Phase | Continuation Phase | Drugs[1b] | Dosing Interval and Doses[1c] (minimum duration) | Total Doses for Both Phases (total minimum duration) |
|---|---|---|---|---|
| | 4a | INH-RIF | 7 days/wk for 217 doses (31 wks) OR 5 days/wk for 155 doses (31 wks)[1d] | 7 days/wk initially = 273 doses OR 5 days/wk initially = 195 doses (total 39 wks) |
| | 4b | INH-RIF | twice weekly for 62 doses (31 wks)[1d] | 7 days/wk initially = 118 doses OR 5 days/wk initially = 102 doses (total 39 wks) |

[1a]Each regimen consists of an initial phase and a continuation phase; Regimen 1 has 3 possible continuation phases (a, b, c), Regimens 2 and 4 have 2 possible continuation phases (a, b), and Regimen 3 has 1 recommended continuation phase (a).
[1b]INH = isoniazid; RIF = rifampin; PZA = pyrazinamide; EMB = ethambutol; RPT = rifapentine
[1c]Daily regimen = 7 days/wk; drugs can be given 5 days/wk if directly observed therapy (DOT) is used (this can be considered a daily regimen and total required number of doses is lowered accordingly). Continuation phase regimens given 2 or 3 times weekly should be given using DOT.
[1d]Patients with cavitation on initial chest radiograph who still have positive cultures at completion of the initial phase (2 months) should receive a 7-month (31-week) continuation phase consisting of 217 doses (7 days/wk) or 62 doses (twice weekly)
[1e]Continuation phase regimens 1b and 2a are not recommended for HIV-infected patients who have CD4+ counts less than 100/mm$^3$
[1f]Continuation phase regimens 1c and 2b should be used only in HIV-negative patients who have negative sputum smears at completion of the initial phase at 2 months (8 wks) and who do not have cavitation on initial chest radiograph. If patients are started on one of these regimens and the 2-month culture is found to be positive, the continuation phase should be extended an extra 3 months.

The term "isotopically labeled" shall mean isotopically labeled with carbon-13, nitrogen-15, sulfur-33, sulfur-34, oxygen-17, oxygen-18 at positions on the compound (exocyclic positions), preferably positions which are involved in reactions which produce toxic adducts to *Mycobacterium*. Each of these isotopes exhibits paramagnetism which responds to a magnetic field pursuant to the present invention. The magnetic field can be positioned on or near the patient in order to facilitate the concentration of isotopically labeled agent in a particular tissue or at a site to enhance biological activity.

Figure 5:
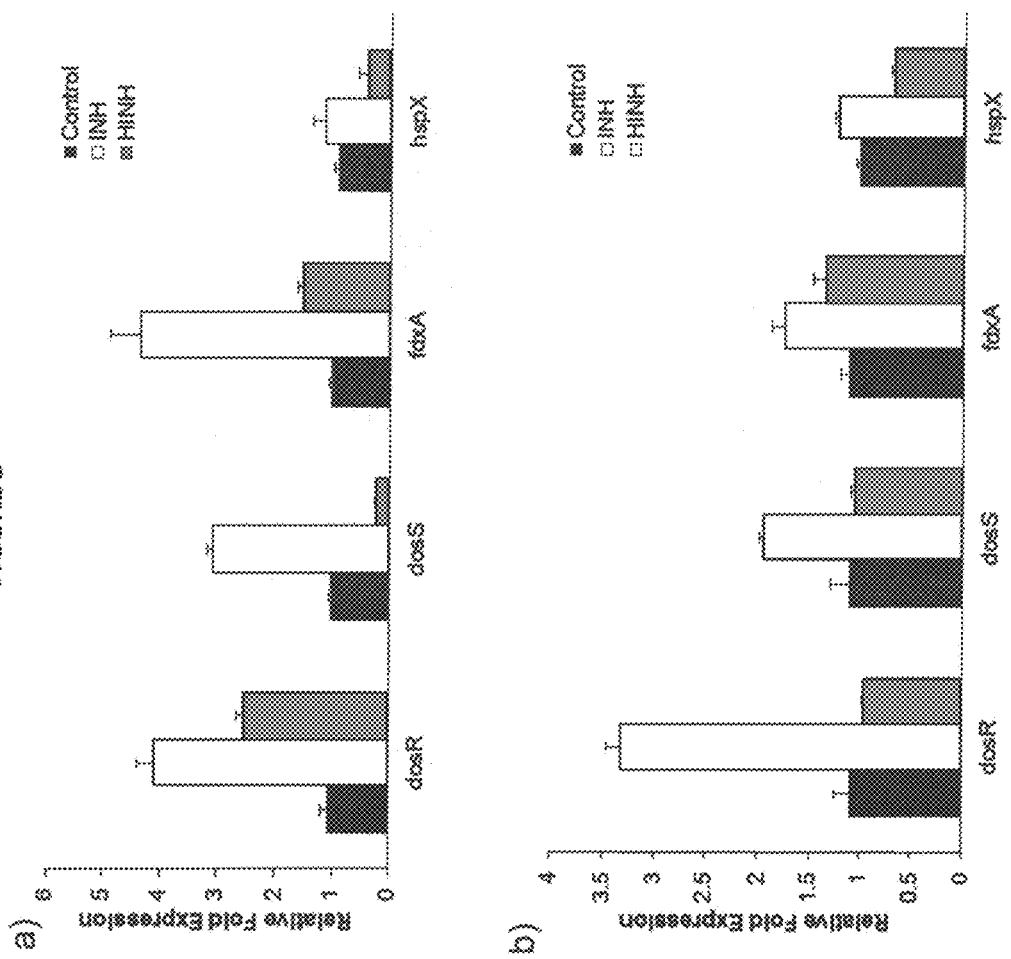
Figure 7A:
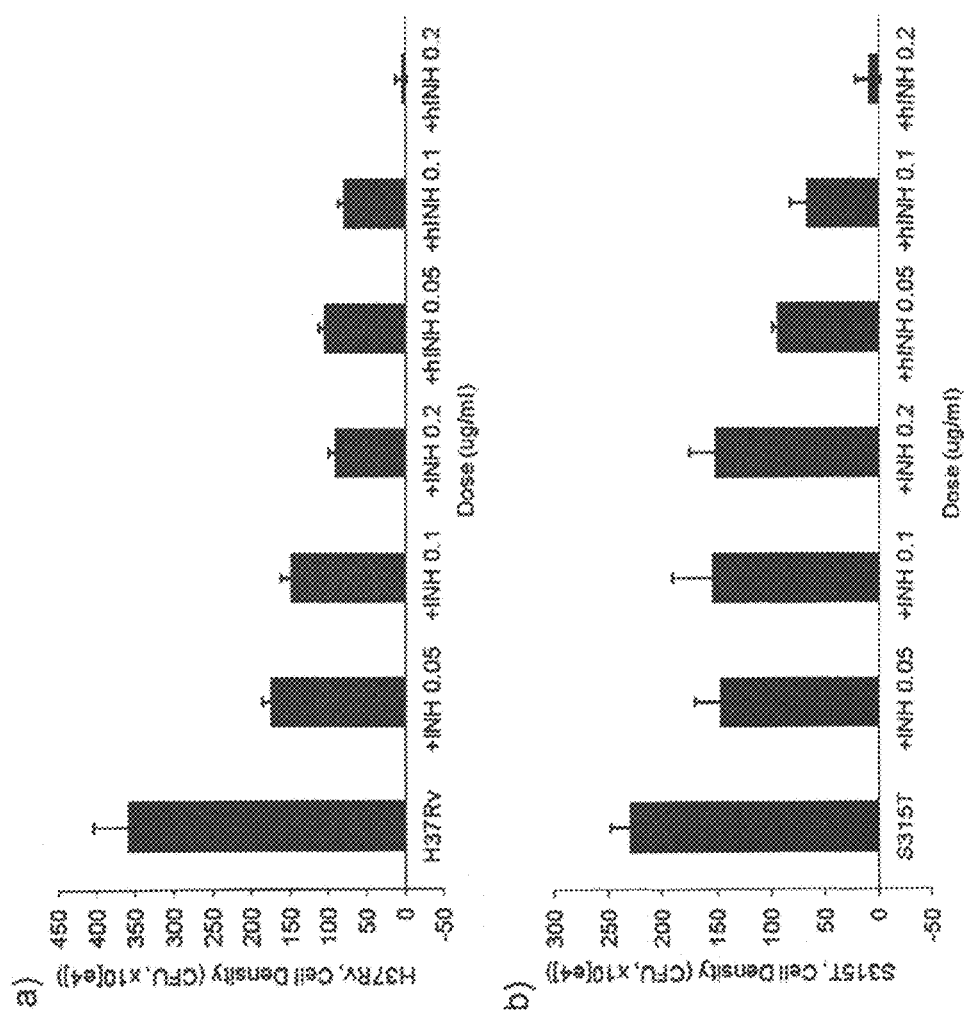
Figure 8:
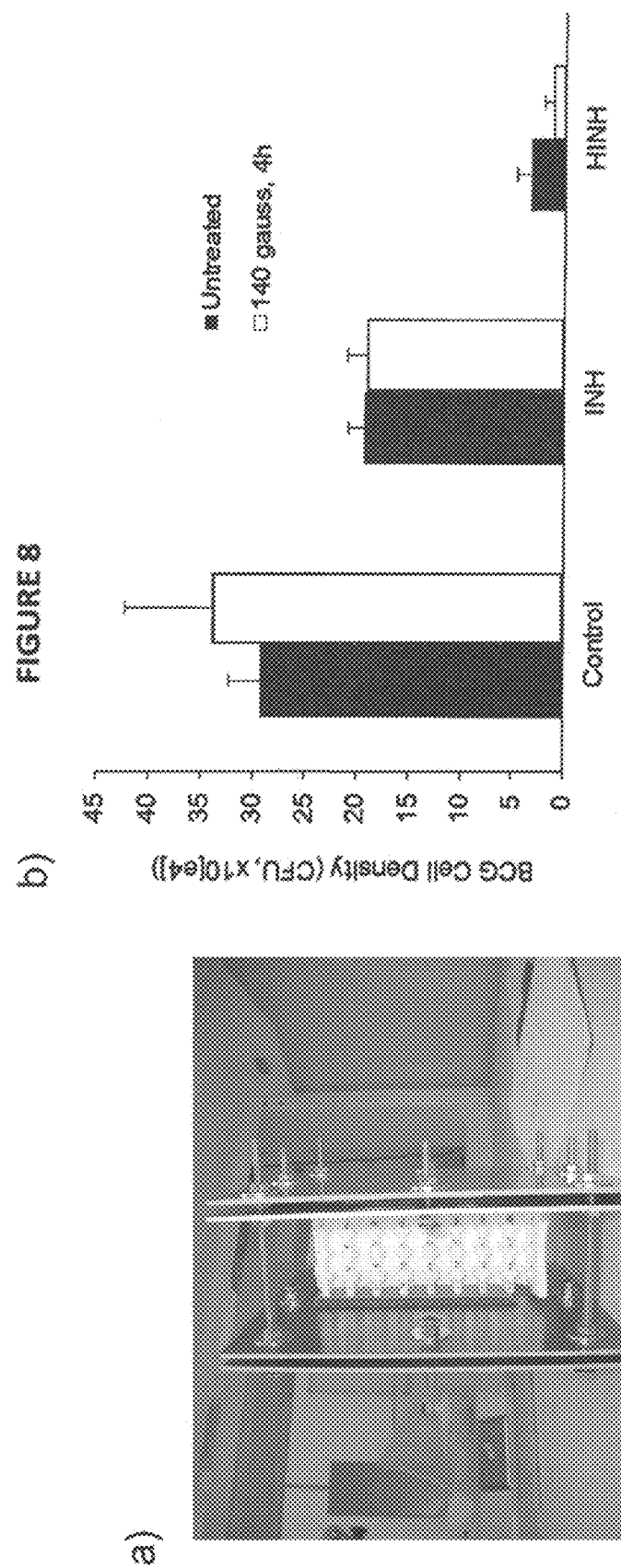
Figure 8:
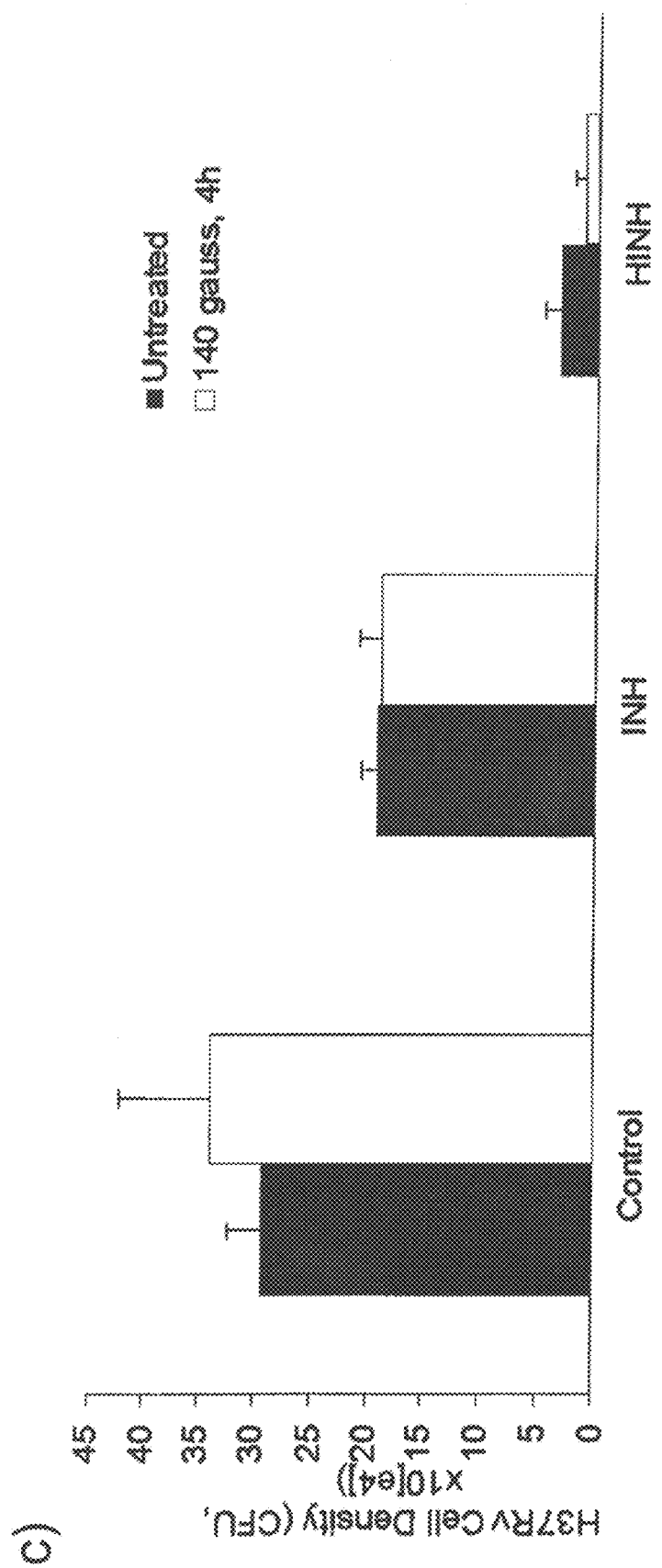
Figure 8A:
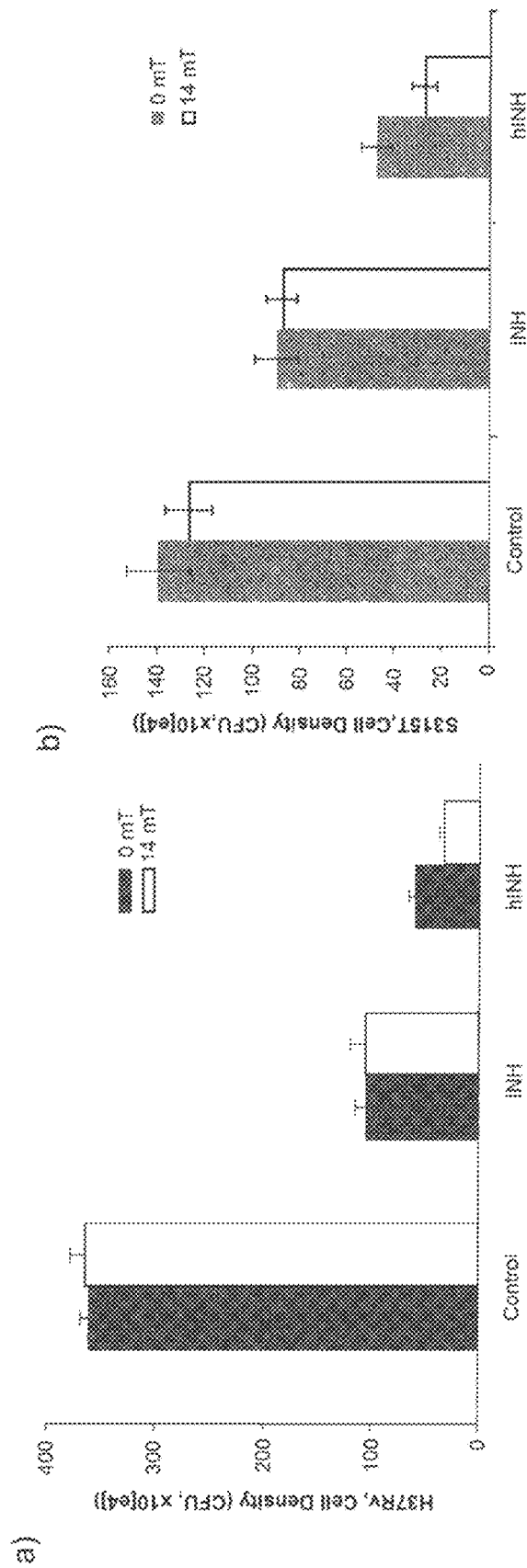
Figure 9:
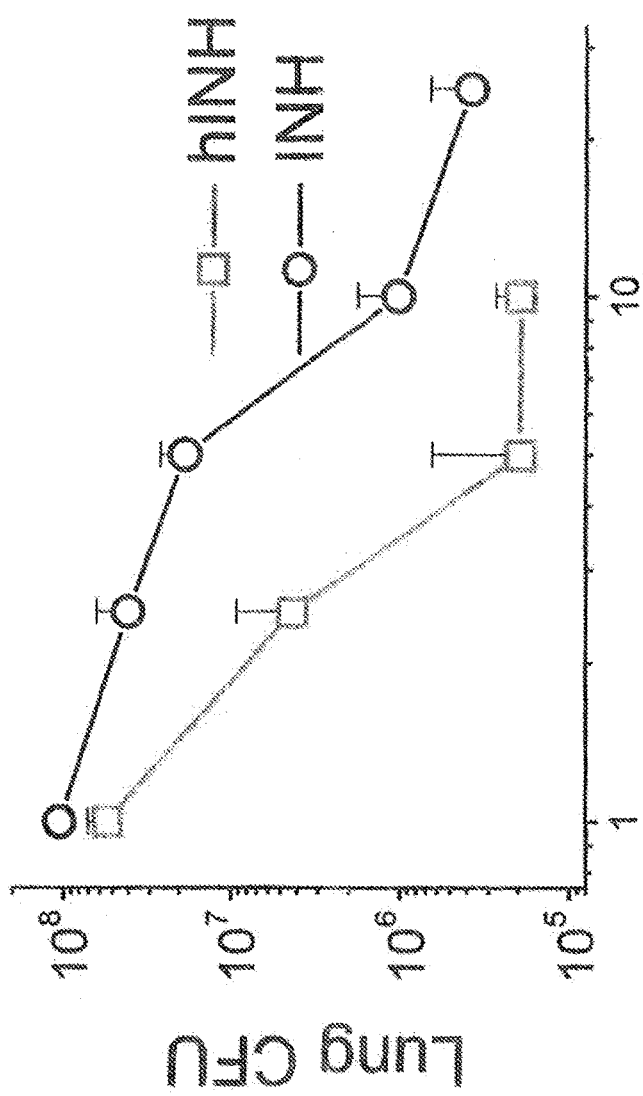
Figure 10:
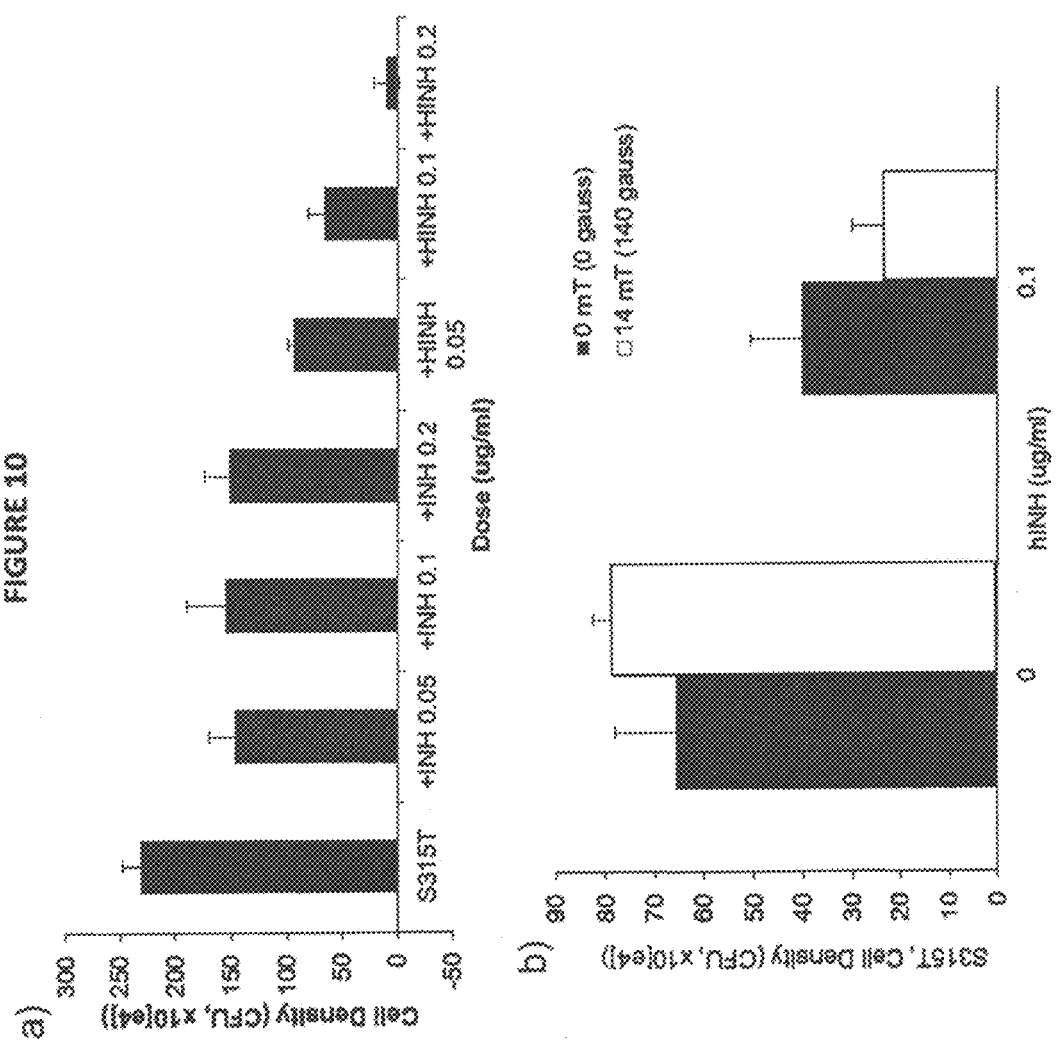
Figure 10A:
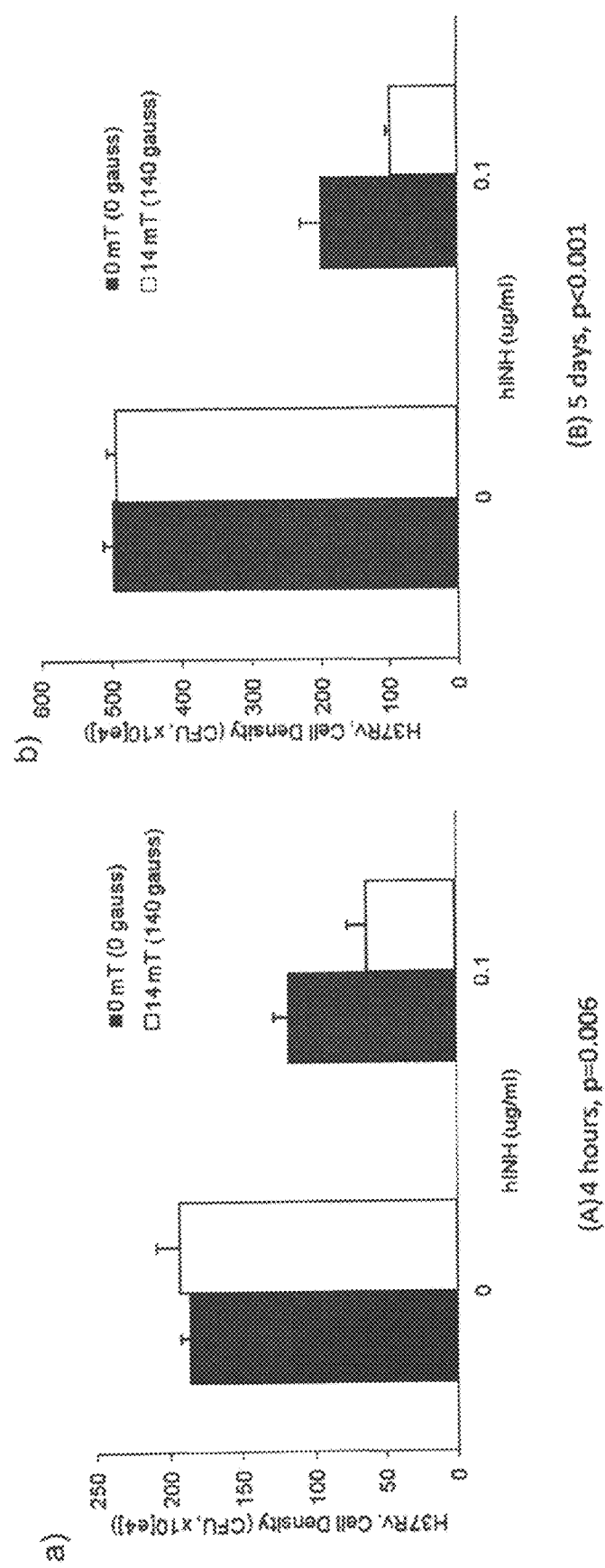
Figure 10B:
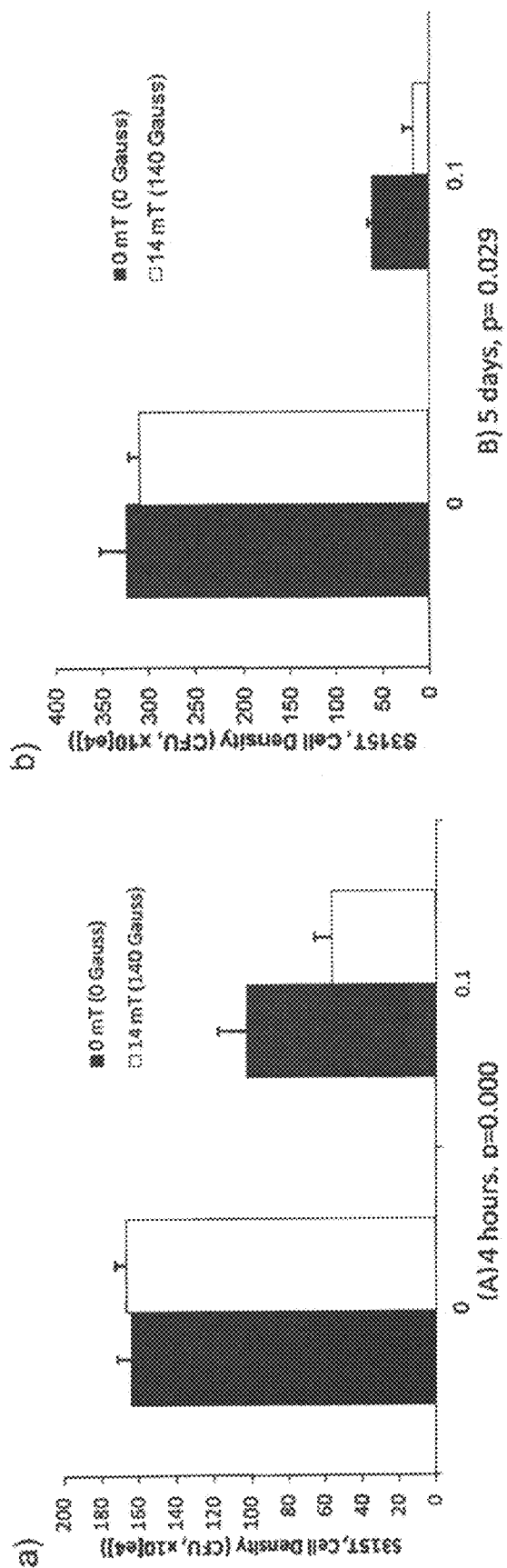

The term "magnet" is used to describe a material that is surrounded by a magnetic field which is natural or induced (e.g. electrically induced) such that the material will attract a paramagnetic material or ferromagnetic material, in the present invention, isotopically labeled compound(s). Magnets for use in the present invention may be permanent or electrically induced (electromagnets). Preferred magnets often are permanent magnets called neodymium magnets (neo magnets). They are a type of rare earth magnets made from an alloy of neodymium, iron and boron. They are currently considered the strongest permanent magnet. The term magnet also refers to electrically induced magnets or electromagnets which can be used to generate electric fields. An electromagnet produces a magnetic field based upon the flow of electric current in proximity to and through the material to be magnetized. An electromagnet may be advantageously used in the present invention and can have the magnetic field adjusted according to the amount of current flowing. The disadvantage of the electromagnet is the requirement for a permanent source of current to produce the electromagnetic field, resulting in logistical problems associated with therapy, particularly in ambulatory patients. Preferred magnets according to the present invention have a magnetic field greater than the Earths magnetic field ranging from about 10 to about 1000 Gauss or more, often about 50-250 Gauss, even more often about 100-200 Gauss, still more often about 140-160 Gauss, and most often has a value of around 150 Gauss. FIG. 5 illustrates the magnetic field strength effect. It is believed that the magnetic field effect begins at around 50 gauss, reaches a maximize value at around 140 G, and begins to taper in the range of about 600-1,000 G. In certain instances, magnetic fields of significantly higher strength may be used (from about 0.1 to about 0.7 Tesla units or about 1,000 to about 7,000 Gauss or more—up to about 1.5 Tesla or 15,000 Gauss depending on the infection, its difficulty in treating and the tissue and location in the tissue in which the infection is found), for example, in instances where administration into the lungs at a particular site is desired or in particularly difficult to treat illness (e.g. multiple drug resistant tuberculosis).

The unit for measuring the magnetic field forces for certain biomedical applications is the Tesla unit (1 Tesla unit corresponds to 10,000 Gauss). Gauss units are used in the CGS system whereas Tesla is applied in the SI system.

The term "*Mycobacterium*", is used to describe a genus of Actinobacteria, given its own family, the Mycobacteriaceae. The genus includes pathogens known to cause serious diseases in mammals, including tuberculosis and leprosy. The Latin prefix "myco" means both fungus and wax; its use here relates to the "waxy" compounds in the cell wall. Mycobacteria are aerobic and non-motile bacteria (except for the species *Mycobacterium marinum* which has been shown to be motile within macrophages) that are characteristically acid-alcohol fast. Mycobacteria do not contain endospores or capsules, and are usually considered Gram-positive. While mycobacteria do not seem to fit the Gram-positive category from an empirical standpoint (i.e. they do not retain the crystal violet stain), they are classified as an acid-fast Gram-positive bacterium due to their lack of an outer cell membrane. All *Mycobacterium* species share a characteristic cell wall, thicker than in many other bacteria, which is hydrophobic, waxy, and rich in mycolic acids/mycolates. The cell wall makes a substantial contribution to the hardiness of this genus.

Many *Mycobacterium* species adapt readily to growth on very simple substrates, using ammonia or amino acids as nitrogen sources and glycerol as a carbon source in the presence of mineral salts. Optimum growth temperatures vary widely according to the species and range from 25° C. to over 50° C.

Some species can be very difficult to culture (i.e. they are fastidious), sometimes taking over two years to develop in culture. Further, some species also have extremely long reproductive cycles: *M. leprae* (leprosy), may take more than 20 days to proceed through one division cycle (for comparison, some *E. coli* strains take only 20 minutes), making laboratory culture a slow process.

A natural division occurs between slowly—and rapidly—growing species. Mycobacteria that form colonies clearly visible to the naked eye within 7 days on subculture are termed rapid growers, while those requiring longer periods are termed slow growers. Mycobacteria are slightly curved or straight rods between 0.2-0.6 μm wide by 1.0-10 μm long.

A "*Mycobacterium* infection" includes, but is not limited to, tuberculosis and atypical mycobacterial infections cause by a *Mycobacterium* species other than *M. tuberculosis*. Atypical mycobacterial infections include, but are not limited to, abscesses, septic arthritis, and osteomyelitis (bone infection). They can also infect the lungs, lymph nodes, gastrointestinal tract, skin, and soft tissues. Atypical mycobacterial infections can be caused by *Mycobacterium avium-intracellulare*, which frequently affects AIDS patients and causes lung disease. *Mycobacterium marinum* cause skin infections and is also responsible for swimming pool granuloma. *Mycobacterium ulcerans* cause skin infections. *Mycobacterium kansasii* causes lung disease.

A particularly important *Mycobacterium* species to the present invention is *M. tuberculosis*. The term "Tuberculosis" or "TB" is used to describe the infection caused by the infective agent "*Mycobacterium tuberculosis*" or "*M. tuberculosis*", a tubercle *bacillus* bacteria. Tuberculosis is a potentially fatal contagious disease that can affect almost any part of the body but is most frequently an infection of the lungs. It is caused by a bacterial microorganism, the tubercle *bacillus* or *Mycobacterium tuberculosis*.

Tuberculosis is primarily an infection of the lungs, but any organ system is susceptible, so its manifestations may be varied. Effective therapy and methods of control and prevention of tuberculosis have been developed, but the disease remains a major cause of mortality and morbidity throughout the world. The treatment of tuberculosis has been complicated by the emergence of drug-resistant organisms, including multiple-drug-resistant tuberculosis, especially in those with HIV infection.

*Mycobacterium tuberculosis*, the causative agent of tuberculosis, is transmitted by airborne droplet nuclei produced when an individual with active disease coughs, speaks, or sneezes. When inhaled, the droplet nuclei reach the alveoli of the lung. In susceptible individuals the organisms may then multiply and spread through lymphatics to the lymph nodes, and through the bloodstream to other sites such as the lung apices, bone marrow, kidneys, and meninges.

The development of acquired immunity in 2 to 10 weeks results in a halt to bacterial multiplication. Lesions heal and the individual remains asymptomatic. Such an individual is said to have tuberculous infection without disease, and will show a positive tuberculin test. The risk of developing active disease with clinical symptoms and positive cultures for the tubercle *bacillus* diminishes with time and may never occur, but is a lifelong risk. Approximately 5% of individuals with tuberculous infection progress to active disease. Progression occurs mainly in the first 2 years after infection; household contacts and the newly infected are thus at risk.

Many of the symptoms of tuberculosis, whether pulmonary disease or extrapulmonary disease, are nonspecific. Fatigue or tiredness, weight loss, fever, and loss of appetite may be present for months. A fever of unknown origin may be the sole indication of tuberculosis, or an individual may have an acute influenza-like illness. Erythema nodosum, a skin lesion, is occasionally associated with the disease.

The lung is the most common location for a focus of infection to flare into active disease with the acceleration of the growth of organisms. Infections in the lung are the primary focus of the present invention. There may be complaints of cough, which can produce sputum containing mucus, pus- and, rarely, blood. Listening to the lungs may disclose rales or crackles and signs of pleural effusion (the escape of fluid into the lungs) or consolidation if present. In many, especially those with small infiltration, the physical examination of the chest reveals no abnormalities.

Miliary tuberculosis is a variant that results from the blood-borne dissemination of a great number of organisms resulting in the simultaneous seeding of many organ systems. The meninges, liver, bone marrow, spleen, and genitourinary system are usually involved. The term miliary refers to the lung lesions being the size of millet seeds (about 0.08 in. or 2 mm). These lung lesions are present bilaterally. Symptoms are variable.

Extrapulmonary tuberculosis is much less common than pulmonary disease. However, in individuals with AIDS, extrapulmonary tuberculosis predominates, particularly with lymph node involvement, with some pulmonary impact. For example, fluid in the lungs and lung lesions are other common manifestations of tuberculosis in AIDS. The lung is the portal of entry, and an extrapulmonary focus, seeded at the time of infection, breaks down with disease occurring.

Development of renal tuberculosis can result in symptoms of burning on urination, and blood and white cells in the urine; or the individual may be asymptomatic. The symptoms of tuberculous meningitis are nonspecific, with acute or chronic fever, headache, irritability, and malaise.

A tuberculous pleural effusion can occur without obvious lung involvement. Fever and chest pain upon breathing are common symptoms. Bone and joint involvement results in pain and fever at the joint site. The most common complaint is a chronic arthritis usually localized to one joint. Osteomyelitis is also usually present. Pericardial inflammation with fluid accumulation or constriction of the heart chambers secondary to pericardial scarring are two other forms of extrapulmonary disease.

At present, the principal methods of diagnosis for pulmonary tuberculosis are the tuberculin skin test (an intracutaneous injection of purified protein derivative tuberculin is performed, and the injection site examined for reactivity), sputum smear and culture, and the chest x-ray. Culture and biopsy are important in making the diagnosis in extrapulmonary disease.

A combination of two or more drugs is often used in the initial traditional therapy of tuberculous disease. Drug combinations are used to lessen the chance of drug-resistant organisms surviving. The preferred treatment regimen for both pulmonary and extrapulmonary tuberculosis is a 6-month regimen of the antibiotics isoniazid, rifampin, and pyrazinamide given for 2 months, followed by isoniazid and rifampin for 4 months. Because of the problem of drug-resistant cases, ethambutol can be included in the initial regimen until the results of drug susceptibility studies are known. Once treatment is started, improvement occurs in almost all individuals. Any treatment failure or individual relapse is usually due to drug-resistant organisms.

Compounds used in the methods of treatment of the present invention may be used in pharmaceutical compositions having biological/pharmacological activity for the treatment of, for example, Mycobacterial infections, including a number of other conditions and/or disease states which may appear or occur secondary to the bacterial infection. These compositions comprise an effective amount of any one or more of the compounds disclosed hereinabove, optionally in combination with a pharmaceutically acceptable additive, carrier or excipient. Compounds used in the methods of treatment of the present invention may also be used as intermediates in the synthesis of compounds exhibiting biological activity as well as standards for determining the biological activity of the present compounds as well as other biologically active compounds.

The compounds used in the methods of treatment of the present invention may be formulated in a conventional manner using one or more pharmaceutically acceptable carriers. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compounds used in the methods of treatment of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally, or intravenously. Preferred routes of administration include oral administration and pulmonary administration (by inhaler/inhalation spray).

Sterile injectable forms of the compounds used in the methods of treatment of the invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed, including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions used in the methods of treatment of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Another suitable administration system could be an inhaled form of hINH or other isotopically labeled compound, such as by dry powder inhaler, or by liquid nebulizer, to achieve high local concentrations within the lung.

Alternatively, the pharmaceutical compositions used in the methods of treatment of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compounds used in the methods of treatment of this invention may also be administered topically, especially when the target of treatment includes areas or organs readily accessible by topical application. Suitable topical formulations are readily prepared for each of these areas or organs.

Topical application also can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions used in the methods of treatment of this invention may also be administered by nasal aerosol or by inhalation into the lungs. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compounds used in the methods of treatment of the instant invention that may be combined with the carrier materials to produce a single dosage form will vary depending upon the host treated, the particular mode of administration. Preferably, the compositions should be formulated so that a therapeutically effective dosage of between about 1 and 25 mg/kg, about 5 to about 15 mg/kg of patient/day of the novel compound can be administered to a patient receiving these compositions. Preferably, pharmaceutical compositions in dosage form according to the present invention comprise a therapeutically effective amount of at least 25 mg of isotopically labeled compound, at least 50 mg of isotopically labeled compound, at least 60 mg of isotopically labeled compound, at least 75 mg of isotopically labeled compound, at least 100 mg of isotopically labeled, at least 150 mg of isotopically labeled compound, at least 200 mg of isotopically labeled compound, at least 250 mg of isotopically labeled compound, at least 300 mg of isotopically labeled compound, about 350 mg of isotopically labeled compound, about 400 mg of isotopically labeled compound, about 500 mg of isotopically labeled compound, about 750 mg of isotopically labeled compound, about 1 g (1000 mg) of isotopically labeled compound, alone or in combination with a therapeutically effective amount of at least one additional anti-tuberculosis agent. Exemplary additional anti-tuberculosis agents which may be used in pharmaceutical compositions include one or more of aminosalicyclic acid/aminosalicylate sodium, capreomycin sulfate, clofazimine, cycloserine, ethambutol hydrochloride (myambutol), kanamycin sulfate, pyrazinamide, rifabutin, rifampin, rifapentine, streptomycin sulfate, gatifloxacin and mixtures thereof, all in therapeutically effective amounts.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

Administration of the active compound may range from continuous (intravenous drip) to several oral or inhalation (intratracheal) administrations per day (for example, B.I.D. or Q.I.D.) and may include oral, pulmonary, topical, parenteral, intramuscular, intravenous, sub-cutaneous, transdermal (which may include a penetration enhancement agent), buccal and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Oral dosage forms are particularly preferred, because of ease of administration and prospective favorable patient compliance.

To prepare the pharmaceutical compositions according to the present invention, a therapeutically effective amount of one or more of the compounds according to the present invention is preferably intimately admixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavoring agents, preservatives, colouring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric-coated or sustained release by standard techniques. The use of these dosage forms may significantly the bioavailability of the compounds in the patient.

For parenteral formulations, the carrier will usually comprise sterile water or aqueous sodium chloride solution, though other ingredients, including those which aid dispersion, also may be included. Of course, where sterile water is to be used and maintained as sterile, the compositions and carriers must also be sterilized. Injectable suspensions may also be prepared, in which case appropriate liquid carriers, suspending agents and the like may be employed.

Liposomal suspensions (including liposomes targeted to viral antigens) may also be prepared by conventional methods to produce pharmaceutically acceptable carriers. This may be appropriate for the delivery of free nucleosides, acyl/alkyl nucleosides or phosphate ester pro-drug forms of the nucleoside compounds according to the present invention.

The present invention also relates to the use of pharmaceutical compositions in an oral dosage form comprising therapeutically effective amounts of isotopically labeled compound according to the present invention, optionally in combination with a pharmaceutically acceptable carrier, additive or excipient. Compositions for oral administration include powders or granules, suspensions or solutions in water or non-aqueous media, sachets, capsules or tablets. Thickeners, diluents, flavorings, dispersing aids, emulsifiers or binders may be desirable.

In preferred aspects of the invention, especially for treatment of *M. tuberculosis* infections, the compound is administered to the lungs of the subject via pulmonary administration, including intratracheal administration. The pharmaceutical composition of the invention for pulmonary administration is usually used as an inhalant. The composition can be formed into dry powder inhalants, inhalant suspensions, inhalant solutions, encapsulated inhalants and like known forms of inhalants. Such forms of inhalants can be prepared by filling the pharmaceutical composition of the invention into an appropriate inhaler such as a metered-dose inhaler, dry powder inhaler, atomizer bottle, nebulizer etc. before use. Of the above forms of inhalants, powder inhalants may be preferable.

When the pharmaceutical composition used in the methods of treatment of the invention is used in the form of a powder, the mean particle diameter of the powder is not especially limited but, in view of the residence of the particles in the lungs, is preferably that the particles fall within the range of about 0.1 to 20 μm, and particularly about 1 to 5 μm. Although the particle size distribution of the powder pharmaceutical composition of the invention is not particularly limited, it is, preferable that particles having a size of about 25 μm or more account for not more than about 5% of the particles, and preferably, 1% or less to maximize delivery into the lungs of the subject.

The pharmaceutical composition in the form of a powder can be produced by, for example, using the drying-micronization method, the spray drying method and standard pharmaceutical methodology well known in the art.

By way of example without limitation, according to the drying-pulverization method, the pharmaceutical composition in the form of a powder can be prepared by drying an aqueous solution (or aqueous dispersion) containing the compound or mixtures with other active agents thereof and excipients which provide for immediate release in pulmonary tissue and microparticulating the dried product. Stated more specifically, after dissolving (or dispersing) a pharmaceutically acceptable carrier, additive or excipient in an aqueous medium, compounds according to the present invention in effective amounts are added and dissolved (or dispersed) by stirring using a homogenizer, etc. to give an aqueous solution (or aqueous dispersion). The aqueous medium may be water alone or a mixture of water and a lower alcohol. Examples of usable lower alcohols include methanol, ethanol, 1-propanol, 2-propanol and like water-miscible alcohols. Ethanol is particularly preferable. After the obtained aqueous solution (or aqueous dispersion) is dried by blower, lyophilization, etc., the resulting product is pulverized or microparticulated into fine particles using jet mills, ball mills or like devices to give a powder having the above mean particle diameter. If necessary, additives as mentioned above may be added in any of the above steps.

According to the spray-drying method, the pharmaceutical composition in the form of a powder of the invention can be prepared, for example, by spray-drying an aqueous solution (or aqueous dispersion) containing isoniazid, urea or mixtures thereof and excipients, additives or carriers for microparticulation. The aqueous solution (or aqueous dispersion) can be prepared following the procedure of the above drying-micronization method. The spray-drying process can be performed using a known method, thereby giving a powdery pharmaceutical composition in the form of globular particles with the above-mentioned mean particle diameter.

The inhalant suspensions, inhalant solutions, encapsulated inhalants, etc. can also be prepared using the pharmaceutical composition in the form of a powder produced by the drying-micronization method, the spray-drying method and the like, or by using a carrier, additive or excipient and isoniazid, urea or mixtures thereof that can be administered via the lungs, according to known preparation methods.

Furthermore, the inhalant comprising the pharmaceutical composition of the invention is preferably used as an aerosol. The aerosol can be prepared, for example, by filling the pharmaceutical composition of the invention and a propellant into an aerosol container. If necessary, dispersants, solvents and the like may be added. The aerosols may be prepared as 2-phase systems, 3-phase systems and diaphragm systems (double containers). The aerosol can be used in any form of a powder, suspension, solution or the like.

Examples of usable propellants include liquefied gas propellants, compressed gases and the like. Usable liquefied gas propellants include, for example, fluorinated hydrocarbons (e.g., CFC substitutes such as HCFC-22, HCFC-123, HFC-134a, HFC-227 and the like), liquefied petroleum, dimethyl ether and the like. Usable compressed gases include, for example, soluble gases (e.g., carbon dioxide, nitric oxide), insoluble gases (e.g., nitrogen) and the like.

The dispersant and solvent may be suitably selected from the additives mentioned above. The aerosol can be prepared, for example, by a known 2-step method comprising the step of preparing the composition of the invention and the step of filling and sealing the composition and propellant into the aerosol container.

As a preferred embodiment of the aerosol according to the invention, the following aerosol can be mentioned: Examples of the compounds to be used include isotopically labeled compound alone or in mixtures with other compounds according to the present invention or with other anti-Mycobacterial agents. As propellants, fluorinated hydrocarbons such as HFC-134a, HFC-227 and like CFC substitutes are preferable. Examples of usable solvents include water, ethanol, 2-propanol and the like. Water and ethanol are particularly preferable. In particular, a weight ratio of water to ethanol in the range of about 0:1 to 10:1 may be used.

The aerosol of the invention contains excipient in an amount ranging from about 0.01 to about $10^4$ wt. % (preferably about 0.1 to $10^3$ wt. %), propellant in an amount of about $10^2$ to $10^7$ wt. % (preferably about $10^3$ to $10^6$ wt. %), solvent in an amount of about 0 to $10^6$ wt. % (preferably about 10 to $10^5$ wt. %), and dispersant in an amount of 0 to $10^3$ wt. % (preferably about 0.01 to $10^2$ wt. %), relative to the weight of compound according to the present invention which is included in the final composition.

The pharmaceutical compositions of the invention are safe and effective for use in the therapeutic methods according to the present invention. Although the dosage of the compounds used in the methods of treatment of the invention may vary depending on the type of active substance administered (isoniazid, ethionamide, propionamide and optional additional anti-tuberculosis agents) as well as the nature (size, weight, etc.) of the subject to be diagnosed, the composition is administered in an amount effective for allowing the pharmacologically active substance to be cleaved to cleavage products to be measured. For example, the composition is preferably administered such that the active ingredient (isotopically labeled compound) can be given to a human adult in a dose of at least about 25 mg, at least about 50 mg, at least about 60 mg, at least about 75 mg., at least about 100 mg, at least about 150 mg, at least about 200 mg, at least about 250 mg, at least about 300 mg, at least about 350 mg, at least about 400 mg, at least about 500 mg, at least about 750 mg, at least about 1000 mg, and given in a single dose, including sustained or controlled release dosages once daily.

The form of the pharmaceutical composition of the invention such as a powder, solution, suspension etc. may be suitably selected according to the type of substance to be administered.

As an administration route, direct inhalation via the mouth using an inhaler is usually administered into the airways and in particular, directly to pulmonary tissue, the active substance contained therein produces immediate effects. Furthermore, the composition is formulated as an immediate release product so that cleavage and analysis can begin soon after administration.

As an administration route, especially for tuberculosis infections, direct inhalation via the mouth using an inhaler is often used. Since embodiments of the pharmaceutical composition of the invention allows direct local administration into the airways and in particular, directly to deep channels of pulmonary tissue, the active substance contained therein produces immediate effects. Furthermore, the composition is formulated preferably as an immediate release product so that cleavage and analysis can begin soon after administration, if desired. Once the composition has been administered (the patient should be placed in the magnetic field at the same time of drug administration), the patient is positioned within a magnetic field created by a permanent magnet as otherwise disclosed herein or an electromagnet positioned in a way to provide a magnetic field to direct the administered compound to the appropriate site of activity within the lungs or other tissue of the patient. This is usually done during administration of the drug and for a period of time thereafter in order to allow the administered compound to be directed to a site of therapeutic activity within the tissue. An electromagnet may be used during administration of the compound and optionally, for a short period thereafter (generally from about a few minutes to an hour or so) and a permanent magnet may be positioned on the patient during administration of the isotopically labeled drug or for a significant period during therapy, which may last a number of weeks or months. In certain embodiments, the magnet creates a gradient field to draw the compound to the proper site within the tissue to be treated.

Compounds used in the methods of treatment according to the present invention may be readily synthesized using methods which are readily available in the art. For example, the compounds may be synthesized by analogy to synthetic approaches which are used to synthesize isotopically labeled isoniazid by modifying the synthetic route which is described in: Schantl J and Gstach H, *Synthesis* (Stuttgart) 1980 (9) pp. 694-695. Other methods are readily available in the art for producing all of the compounds which are described herein.

Starting from pyridine (isoniazid) or 2-alkylpyridine (ethionamide) an ice cooled solution of $Br_2$ neat or in solvent is made. To this a solution of benzophenone-arylhydrazone in absolute (methylene chloride) is added dropwise over a period of approximately 30 minutes at 0-5° C. Seeding crystals of the intermediate salt is made, to which is added isotopically labeled (e.g. carbon-13) potassium cyanide. The cyanide is introduced in the 4-position (para) of the pyridine or alkylpyridine. The isotopically labeled 4-cyano-2-alkylpyridine compound may be further modified to isotopically labeled isoniazid, ethionamide or its derivatives. The resulting compound may have isotopically labeled atoms at virtually every point in the molecule, but preferably has isotopically labeled atoms in the acylhydrazide or thionamide group, because these are the groups are shown to significantly influence the activity of isotopically labeled compounds according to the invention.

There are multiple ways to make ethionamide from the cyanopyridine, such that various positions in the molecule is isotopically labeled. Characterization is by TLC against known standards and by NMR.

Chemical Synthesis

Preparation of $^{13}C$ Acyl isoniazid is via a modification of the method of Feely and Beavers *J. Am. Chem. Soc.* 1959, 81, 4004-4007. 4-[$^{13}C$]cyanopyridine: The synthesis of 1-(n-nonyloxy)-pyridinium iodide was accomplished according to the method of Feely and Beavers. The subsequent method for the generation of the cyanopyridine was modified as follows. $Bu_4N^{13}CN$ (3.00 g, 11.1 mmol) was dissolved in 20 mL of $H_2O$ at room temperature. A solution of 1-(n-nonyloxy)-pyridinium iodide (3.90 g, 11.1 mmol) in 13 mL of $H_2O$ was added and a bright yellow frothy layer separates over a period of a few minutes. The water layer was monitored by $^{13}C$ NMR and after 24 h the relative amount of $Bu_4N^{13}CN$ in solution is minimized and stable. $Et_3N$ (0.9 mL) was added and the mixture was stirred 5 min, then extracted with $CH_2Cl_2$. The combined organic extracts were extracted with 1M HCl, following which the combined acidic extracts were neutralized with conc'n $Na_2CO_3$ in $H_2O$ and again extracted with $CH_2Cl_2$. The organic layer was dried ($Na_2SO_4$), filtered, and the solvent was evaporated. The crude material was purified by column chromatography (10% EtOAc in hexanes) to give 480 mg (41% yield) of product as a white crystalline solid, Mp 77.5-79.5° C. (Lit.[1] 78-80° C.). $^1H$ NMR matched literature values; $^{13}C$ NMR ($CDCl_3$) δ 150.8 (d, J=4.9 Hz), 125.2 (d, J=2.0 Hz), 120.5 (d, J=81.7 Hz), 116.4; Anal. Calcd for $C_5^{13}CH_4N_2$: C, 69.51; H, 3.84; N, 26.65. Found: C, 69.45; H, 3.73; N, 29.26. HRMS m/z 106.04800 (M+1 for M=105.04). Alternatively, the ethylpyridinium chloride, and potassium cyanide have been used.

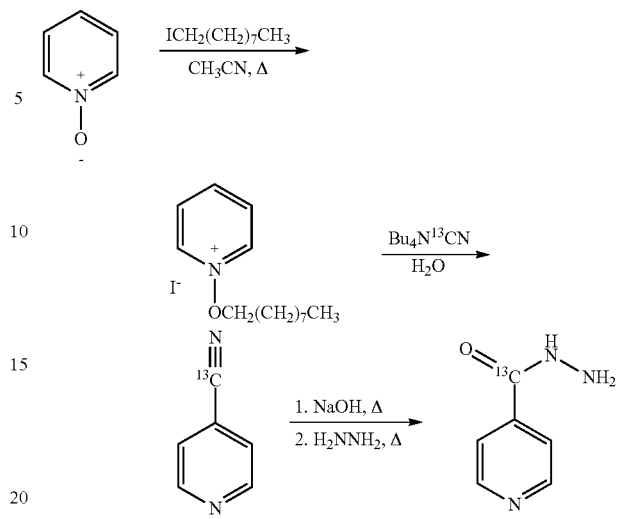

An alternative to the above method for cyanopyridine synthesis is derived from the synthetic route in: Schantl J and Gstach H, *Synthesis* (Stuttgart), 1980 (9) pp 694-695.

An ice cooled solution of $Br_2$ (9.99 g, 62.5 mmol) in absolute pyridine (35 ml) is made. To this a solution of benzophenone-arylhydrazone (62.5 mmol) in absolute $CH2Cl2$ (70 ml) is added drop wise over 30 minutes at 0-5° C. Continue stirring over ice for a further 30 minutes. To this, add 300 ml absolute Ether, and stir with ice, cooling for 90 minutes.

To make seeding crystals, take 2 ml of reaction mixture, add ether and scratch. Add seed crystals to major portion, harvest by filtration. Wash crystals with ether (~250 ml) remove solvent under vacuum. Yield 97%.

The above salt (5.42 mmol) is overlaid with ether (30 ml), KCN (1.41. g) in 5 ml water is added, and the phases mixed vigorously with a flask shaker. The solid phase will disappear of 10-30 minutes. To this then add a further 10 ml of water, and rotary evaporate off the ether. The remaining mix of a yellow oil and water is shaken for 5 hours, will decolorize as cyanopyridine and the benzophenonearylhydrazone reform. (This happens faster if catalytic alkali sodium ethoxide/ethanol is added). The resultant crystals of the benzophenonehydrazone are removed by filtration.

The water solution is saturated with NaCl, 40 mg activated charcoal added, and mixed 10 mins, and filtered through celite. The filtrate is extracted 4×25 ml with Ether, the organic layers pooled, dried with magnesium sulfate, and dried to produce 4-cyanopyridine. This is washed with petroleum ether (40-60° C. fraction) and dried. Yield—75%.

There are multiple ways to make isoniazid from the cyanopyridine. One can use Nguyen et al (*Chembiochem* 2001 2 877-883) a modification of Gasson's synthesis (USPTO 2830994). Characterization was by TLC against known standards and by NMR. Acyl $^{17}O$ or $^{18}O$ can be incorporated by use of $H_2^{17}O$ or $H_2^{18}O$ at this time, either with $^{13}C$ enrichment or independently, if desired. $^{15}N$ may be introduced through the 4-cyano group or an isotopically labeled hydrazine precursor which can be added to form the acyl hydrazide.

As an example, Isoniazid is well synthesized by this procedure:

4-pyridine-[$^{13}C$]carboxylic acid hydrazide

4-[$^{13}C$]Cyanopyridine (400 mg, 3.80 mmol) was combined with 0.6 mL of $H_2O$. The slurry was heated to 40° C.

and aq. NaOH (8%, 0.125 mL) was added dropwise over 30 min. After the slurry formed a slightly yellow solution it was heated to reflux for 1 h. The solution was cooled to ~90° C. and H$_2$NNH$_2$ (65-68% in H$_2$O, 0.75 mL, ~15 mmol) was carefully added dropwise over 20 min. Heated the solution to 104° C. for 3 h. The mixture was then cooled the solvent evaporated. The residue was taken up in a minimum amount of boiling methanol and activated charcoal was added. The hot mixture was filtered and cooled to 0° C. overnight. Precipitated crystals were recovered by filtration and washed with ice cold methanol. After drying under vacuum, 180 mg (34% yield) of product was obtained as clear needles, Mp 169.0-171.0° C. (Lit. 171-173° C.). Concentration of the mother liquor and recrystallization provided an additional 39 mg (7.4%, 41% total yield) of product with identical melting point. $^1$H NMR matched literature values; $^{13}$C NMR (D$_2$O) δ 170.3, 149.2 (d, J=3.6 Hz), 141.0 (d, J=61.9 Hz), 121.6 (d, J=2.2 Hz); Anal. Calcd for C$_5$$^{13}$CH$_7$N$_3$O: C, 52.89; H, 5.11; N, 30.42. Found: C, 52.67; H, 5.09; N, 33.98. HRMS m/z 139.06944 (M+1 for M=138.06).

Isotopically labeled ethionamide may be made by analogy from the 4-cyanopyridine derivative (with 2-alkyl substitution) using H$_2$$^{33}$S or H$_2$$^{34}$S to introduce the isotopically labeled sulfur at the thioamide position and $^{15}$N may be introduced through the 4-cyano group or through isotopically labeled $^{15}$NH$_3$. Thus, the starting material would alternately be (compared to isoniazid) 2-alkyl-pyridine-N-oxide (where alkyl=C$_1$ to C$_3$), producing the analaogous cyanaopyridine. Treatment with H$_2$S affords the labeled Ethionamide.

A wide variety of magnetic field-inducing apparatus are known to those of ordinary skill in the art and are useful in the methods of treatment described herein, e.g. a nuclear magnetic resonance (NMR) spectrometer (see e.g. US20120212224) and other devices as disclosed in US20130156792 and US 20060142749.

These and other aspects of the invention are illustrated in the following non-limiting example.

Example 1

Materials and Methods

CO Detection

INH was mixed with 1 mM tert-butyl hydroperoxide (t-BHP) and KatG at 0.448 ug/ul in 10 mM phosphate buffer, pH 7. The reaction mixture was incubated at 37° C. for 5 mM. 200 ul of deoxyMyoglobin (dMb) containing 0.04% Na2S2O4 was added into the reaction mixture to trap CO. The concentration of CO-trapped myoglobin (MbCO) was calculated by measuring absorbance at 540 nm (ε=15.4/mM cm).

Isotope Ratio Mass Spectrometry (IRMS) was used to detect directly CO released from INH. 50 ug of INH or hINH was incubated with 540 nM Mn pyrophophate. Head gas in reaction mixture was collected, and 13C enrichment in CO was measured by IRMS.

Expression of Dos Regulon

Mtb H37Rv and M. bovis BCG were incubated with INH or hINH for 4 h. Real Time PCR was performed using 2~8 ng RNA, 280 nM Primers, and 7500 Fast Real Time system. Relative quantitative analysis (ddCt) was done using SDS software of Applied Biosystems Inc.

Survival Assay

Mtb H37Rv, M. bovis BCG, and/or H37Rv S315T (KatG mutant) were treated with INH or hINH. At Day 5 part of culture was taken, diluted in PBS/0.05% Tween80, plated on 7H10 plates for 21 days, and CFUs counted. To confirm the MIE, hINH and INH were used to treat Mtb H37Rv, M. bovis BCG, and H37Rv S315T under a static magnetic field (14 mT) and CFUs compared.

Animal Experiment

Mice (groups of 5) were aerosol infected with Mtb H37Rv, and treated daily by gavage (5 days/week) with INH or hINH. At 28 days treatment, animals were sacrificed and lungs plated for CFU.

Statistical Analysis

Statistical significance was evaluated by one-way ANOVA and Tukey as a post hoc (n=3~4) unless otherwise mentioned.

Background

Isoniazid (INH) is a pro-drug that is activated by catalase peroxidase (KatG) of *Mycobacterium tuberculosis* (Mtb) to produce isonicotinyol (INacyl) radicals: these then react with NAD to produce mycolate synthesis inhibitors. We found that INacyl radicals also decompose to release CO, and so lose the ability to produce INacyl-NAD adducts. Since CO induces dormancy in Mtb, we hypothesized that reducing this decarbonylation by selective 13C substitution (to produce heavy isoniazid, hINH) would increase activity of the resultant drug by maximizing INacyl-NAD formation, and minimizing dormancy induction by CO. Here, we describe how this 13C magnetic isotope effect (MIE) can produce more effective drugs.

Methods

INH was activated with Mn(III) pyrophosphate, H2O2 or KatG with tert-butyl hydroperoxide. CO was trapped by Myoglobin (Mb). As shown in FIG. 1, MbCO was formed by CO released from INH. deoxyMb-containing Na$_2$SO$_4$ (A, 0.004%; B, 0.1%) was flushed with CO gas as indicated. NAD or hINH was co-incubated to inhibit CO-Mb formation. CO released from INH or hINH was measured by Isotope Ratio Mass Spectrometry (IRMS). M. bovis BCG and Mtb H37Rv were incubated with INH or hINH, and RNA expression of dos regulons was examined by Real Time PCR. After 5 days of treatment with INH or hINH, colony forming units (CFU) of M. bovis BCG and Mtb H37Rv was compared. To confirm the MIE, hINH and INH were used to treat M. bovis BCG under a static magnetic field (14 mT, 4 hours) and CFUs compared.

Results

1) CO was produced from activated INH or hINH dependent upon dose, time, and KatG. MbCO was formed by CO released from INH. Referring to FIG. 1, deoxyMb containing Na$_2$S$_2$O$_4$ (A, 0.004%; B, 0.1%) was flushed with CO gas as indicated. 10 µmM INH was mixed with KatG at 0.448 µg/µl, 1 mM tBHP in 10 mM phosphate buffer, pH7. The reaction mixture was incubated at 37° C., 5 min. and placed on ice. 200 µl of deoxyMyoglobin (dMb) containing 0.04% Na$_2$S$_2$O$_4$ was added into the reaction mixture to trap CO. The concentration CO-trapped myoglobin (MbCO) was calculated by measuring the change in absorbance at 540 nm (ε=15.4/mM·cm).

Figure 2:
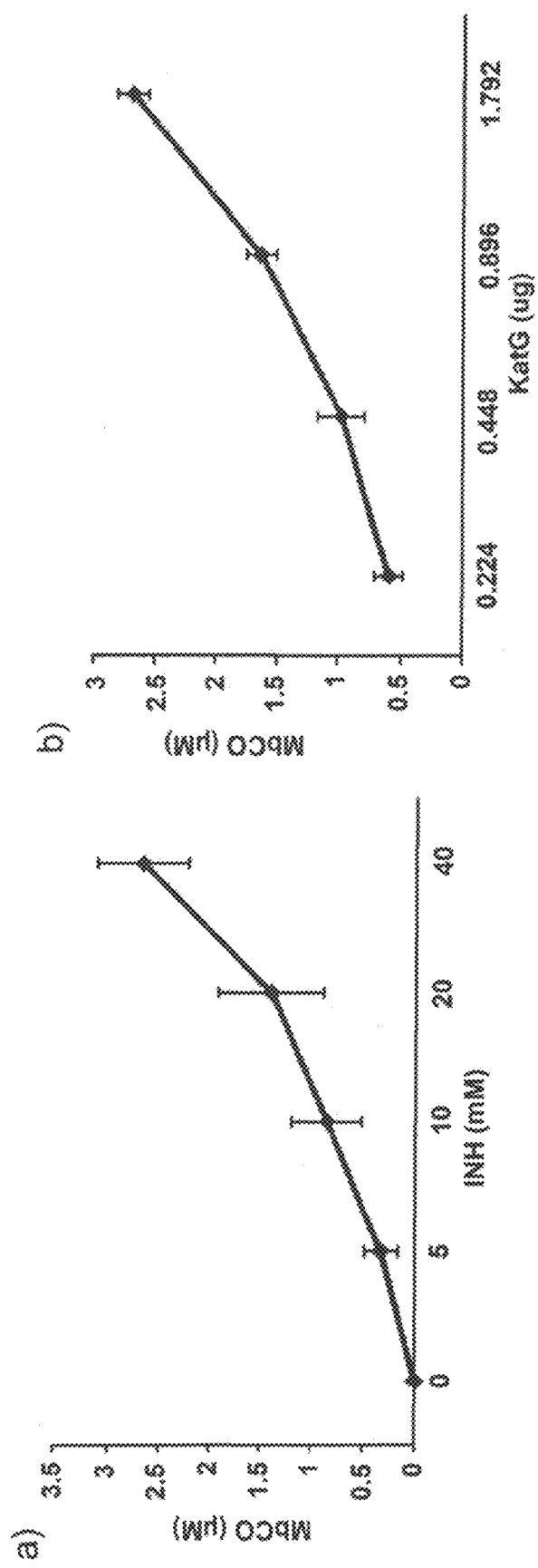

2) $^{13}$CO released from hINH was detected by IRMS (see FIGS. 1 and 2). CO release was dependent on INH or KatG amount, as shown in FIG. 2. Referring to FIG. 2, various amounts of INH or KatG were mixed with 1 mM tBHP and KatG at 0.448 µg/µl in 10 mM phosphate buffer, pH 7, 50 µl on ice. The reaction mixture was incubated at 37° C., 5 min. and then placed on ice. 200 μL of deoxyMycglobin (dMb) containing 0.04% $Na_2S_2O_4$ was added into the reaction mixture to trap CO. The concentration of CO-trapped myoglobin (MbCO) was calculated by measuring the change in absorbance at 540 nm ($\epsilon$=15.4/mM·cm). $p<0.01$ by ANOVA-Tukey (n=3).

Figure 3:
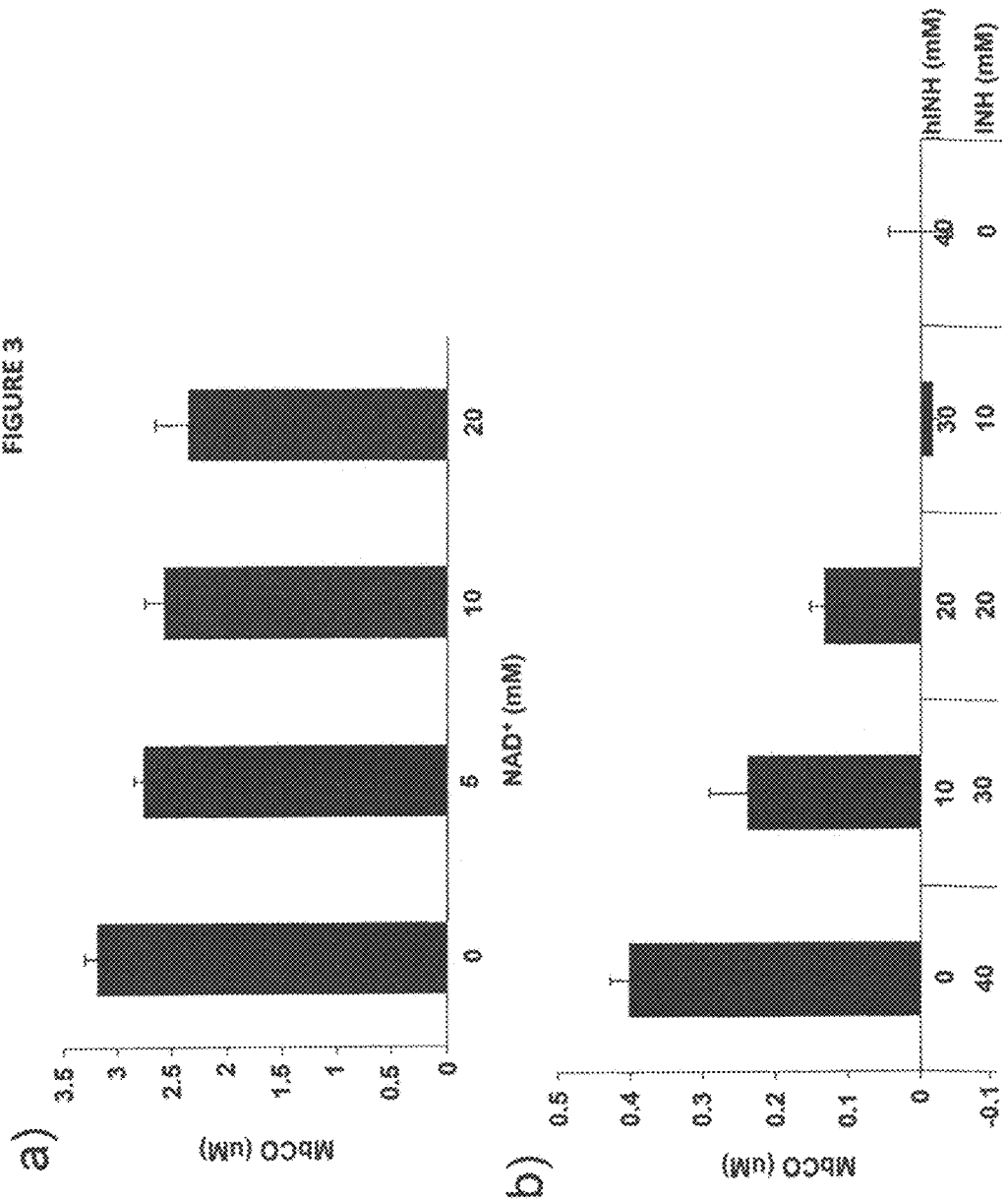

3) CO-Mb formation was inhibited by NAD (see FIG. 3). NAD+ or hINH inhibited the formation of MbCO, as shown in FIG. 3. Referring to FIG. 3, various dosages of NAD+ (A) or hINH (B) were incubated with Kat G at 22.44 μg per reaction, and 1 mM tBHP in 10 mM phosphate buffer, pH 7. the reaction mixture was incubated at 37° C., 5 min. before adding 200 μl of deoxyMyoglobin (dMb) containing 0.04% $Na_2S_2O_4$ and incubated at RT overnight. The concentration of CO-trapped myoglobin (MbCO) was calculated by measuring the change in absorbance at 540 nm ($\epsilon$=15.4/mM·cm). $p<0.05$ by One-way ANOVA-Tukey (n=3).

Figure 4:
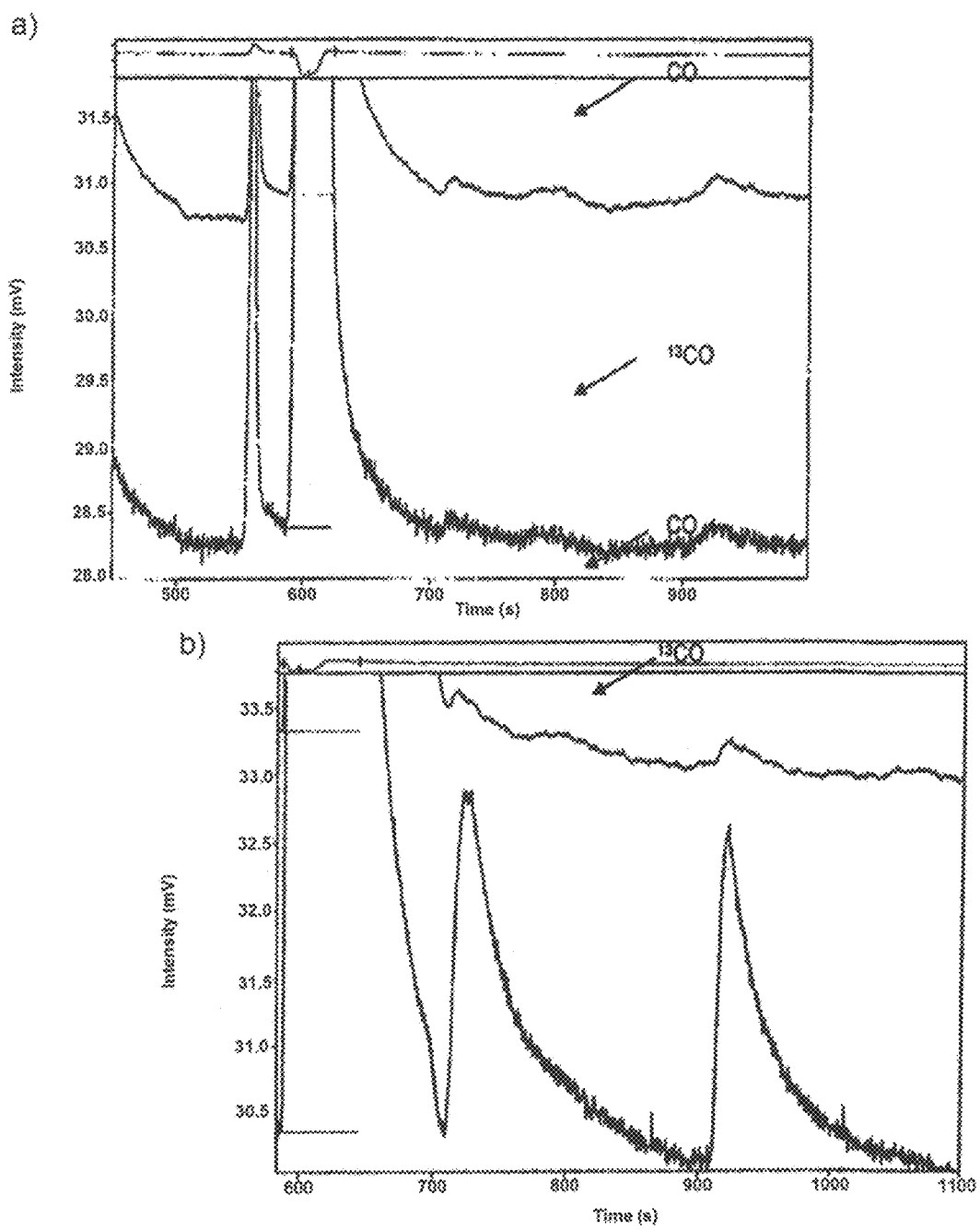
Figure 4:
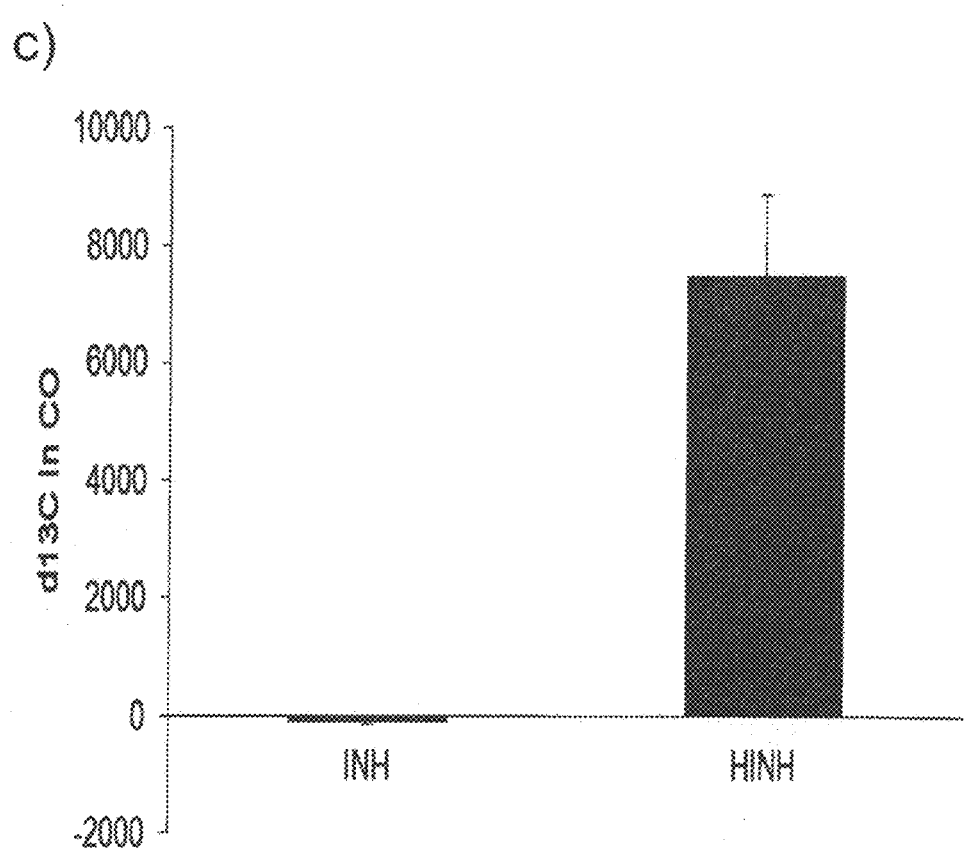

4) CO release from activated hINH was much less than from INH (see FIG. 4). CO released from INH or hINH was detected by Isotope Radio Mass Spectrometry, as shown in FIG. 4. Referring to FIG. 4, 50 μg of INH (A) or hINH (B) were incubated with 540 MnPP in 0.5 ml. CO was separated by Mol sieve 5A column. 13C enrichment in CO is shown by d13C [rR29/28(sample)−rR29/R28(control gas)]/rR29/R28(control gasX 1,000. rR: raw Relative peak area. Numbers are mean±STD (n=3). $p<0.001$ by Student's t-test.

Figure 11:
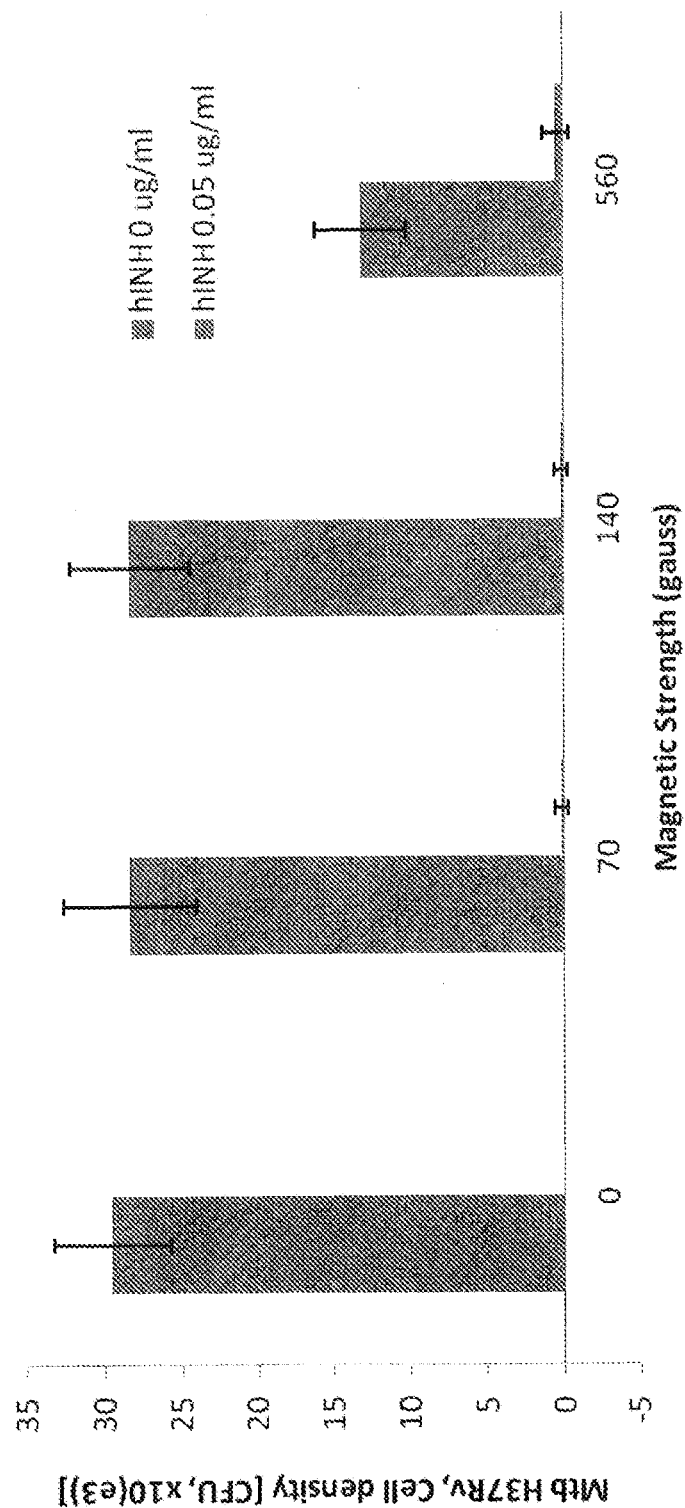

5) The expression of dos regulon genes (dosR, dosS, fdxA) was significantly increased by NH, but not hINH (see FIG. 5 and Table 1 below). FIG. 5 shows Real time PCR measurement of RNA (transcript) levels of dormancy genes in *M. bovis*. BCG (A)/Mtb H37Rv (B) treated with INH or hINH for 4 hours. Referring to FIG. 5, Real Time PCR was performed using 28 ng RNA, 280 nM primers and 7500 Fast Real time system and Relative Quantitation analysis (ddCt) was done using SDS software of Applied Biosystems Inc. SigA was used as the endogenous control to normalize expression values and samples of Control (Non-treatment) were used as calibrator to calculate fold induction. $p<0.01$ by One-way ANOVA-Tukey (n=3).

TABLE 1

Does hINH downregulate dos regulon in Mtb H37Rv?
Effect of hINH on gene expression: RNA microarray

| Rv Number | nINH/INH | +CO/−CO* | Gene | Rv Number | nINH/INH | +CO/−CO* | Gene |
|---|---|---|---|---|---|---|---|
| Rv0079 | −2.3 | 3.3 | | Rv2028 | 1.3 | 1.9 | |
| Rv0080 | — | 2.9 | | Rv2029 | −1.5 | 6.6 | pkfB |
| Rv0081 | −2.5 | 2.3 | | Rv2030 | −3.4 | 9.2 | |
| Rv0669 | 1.2 | 6 | | Rv2031 | −14 | 5.2 | hsoX (acr) |
| Rv0670 | −1.5 | 3.2 | nroZ | Rv2032 | −2.0 | 8.4 | acg |
| Rv0671 | — | 2.3 | | Rv2823 | −2.3 | 6.8 | TB31.7 |
| Rv0672 | −3.0 | 2.8 | | Rv2824 | 1.7 | 7.1 | |
| Rv0673 | — | 1.5 | pncB2 | Rv2825 | 2.2 | 2.2 | |
| Rv0674 | — | 1.7 | | Rv2826 | — | 10 | hrp1 |
| Rv1733 | −2.2 | 2.3 | | Rv2827 | 1.9 | 4.2 | |
| Rv1734 | — | 2 | | Rv2828 | 2.1 | 6.8 | |
| Rv1735 | −1.6 | 1.6 | | Rv2829 | −2.1 | 2.6 | |
| Rv1736 | −2.3 | 2.4 | narX | Rv2830 | −7.3 | 5.2 | |
| Rv1737 | −3.1 | 2.1 | narK2 | Rv2831 | −1.4 | 2.7 | |
| Rv1738 | −2.1 | 5.8 | | Rv3126 | 1.6 | 1.8 | |
| Rv1812 | −3.0 | 1.9 | | Rv3127 | 2 | 2.7 | |
| Rv1813 | −1.8 | 5.1 | | Rv3128 | −2.4 | — | |
| Rv1996 | −1.8 | 2.4 | | Rv3129 | 2.5 | — | |
| Rv1997 | 1.3 | 6.8 | ctpF | Rv3130 | — | 11 | tgs1 |
| Rv2003 | — | 3.3 | | Rv3131 | −1.6 | 3.3 | |
| Rv2004 | −3.3 | 4.8 | | Rv3132 | −3.3 | 3.1 | dos8 (devS) |
| Rv2005 | −2.2 | 6.7 | | Rv3133 | −10 | 3 | dosR (devR) |
| Rv2006 | 1.2 | 2.6 | otsB1 | Rv3134 | −1.4 | 7.1 | |
| Rv2007 | — | 7.1 | foxA | | | | |

Kumar et al. HO1-derived CO Induces the *M. turberculosis* Dormancy Regulon *J Biol Chem*. 2008 283: 18032.

6) hINH was more active than INH against *M. bovis* BCG and Mtb H37Rv (see FIGS. 6, 7 and 7A). Referring to FIG. 7A, Mtb culture was treated with INH or hINH at the indicated dosage. At Day 5, 30 μs of culture was diluted with PBS/0.05% Tween80 and plated on 7H10 plates for 21 days. Statistical significance between the groups were compared by ANOVA-Tukey ($p<0.001$, n=3).

7) hINH and INH activity was dependent upon KatG.

8) An applied magnetic field substantially increased the activity of the isotopically labeled compound. hINH killing of Mtb was significantly enhanced by treatment at a magnetic field of 14 mT, whereas INH was not (see FIGS. 8, 8A, 10, 10A and 10B). Referring to FIG. 8A, MTB H37Rv or 315T was treated with hINH at 0.1 ug/ml, placed under MF at 140 gauss (14 mT) for 5 days. Thirty uls of culture dilute in PBS/0.05% Tween80 was plated on 7H10 agar plate and incubated for 21 days. $p<0.001$ (hINH) by ANOVA-Tukey (n=3) H37Rv is an INH sensitive strain, S315T is an NH-resistant strain with a KatG mutation S315T.

Referring to FIG. 10A, Mtb H37Rv was treated with hINH at 0.1 ug/ml, placed under MF at 140 gauss for 4 hours (A) or 5 days (B). Thirty Ws of culture dilute in PBS/0.05% Tween80 was plated on 7H10 agar plate and incubated for 21 days. $p<0.01$ (hINH) by 2-way ANOVA (n=3). H37Rv is an INH sensitive strain. Referring to FIG. 10B, Mtb S315T was treated with hINH at 0.1 ug/ml, placed under MF at 140 gauss for 4 hours (A) or 5 days (B). Thirty uls of culture dilute in PBS/0.05% Tween80 was plated on 7H10 agar plate and incubated for 21 days. $p<0.05$ (hINH) by 2-way ANOVA (n=3). H37Rv is an INH sensitive strain, S315T is an NH-resistant strain with a KatG mutation S315T.

9) hINH was significantly more active than INH in 28 day monotherapy of mice infected with Mtb H37Rv (see FIG. 9). Referring to FIG. 9, mice (groups of 5) were aerosol infected with Mtb H37Rv and treated daily by gavage (5 days/week)

with INH or hINH. At 28 days treatment, animals were sacrificed and lungs (left) plated for CFU. N=5±1 SD. FIG. 11 illustrates the effect of magnetic field on hINH. Mtb H37Rv was treated with hINH at 0.05 ug/ml, placed under various magnetic fields for 5 days. Thirty uls of culture dilute in PBS/0.05% Tween80 was plated on 7H10 agar plate and incubated for 21 days. Statistical significance was examined by two-way ANOVA with post hoc Tukey (n=6, 3 biological replicates with 2 repeats). p<0.001 (untreated vs. hINH treated). p<0.001 (560 gauss vs. other).

CONCLUSION

This study shows that using isotopically labeled anti-tuberculosis compounds enhances drug action over a non-isotopically labeled compound and that this activity may be further markedly enhanced by exposing compound to a magnetic field. Since hINH activity is higher, while drug-induction of dormancy lower, the application of a magnetic field to this therapeutic approach may readily enable a more rapid treatment than INH-containing drug regimens.

What is claimed is:

1. A method of treating a patient or subject for a tuberculosis infection, the method comprising administering to said patient or subject an effective amount of isotopically labeled isoniazid to said patient or subject and exposing said patient or subject to a magnetic field, wherein the magnetic field ranges from 10 to 1,000 Gauss.

2. The method according to claim 1 wherein said administration of said isoniazid and said exposure of said patient or subject to a magnetic field occur at the same time.

3. The method according to claim 1 wherein said administration of said isoniazid and said exposure of said patient or subject to a magnetic field occur within 24 hours of each other.

4. The method according to claim 1 wherein said administration of said isoniazid and said exposure of said patient or subject to a magnetic field occur within 12 hours of each other.

5. The method according to claim 1 wherein said administration of said isoniazid and said exposure of said patient or subject to a magnetic field occur within 6 hours of each other.

6. The method according to claim 1 wherein said administration of said isoniazid and said exposure of said patient or subject to a magnetic field occur within 1 hour of each other.

7. The method according to claim 1 wherein said isoniazid compound is $^{13}$C-acyl isoniazid (hINH).

8. The method according to claim 1 wherein at least one of the exocyclic nitrogen atoms of isoniazid is isotopically labeled.

9. The method according to claim 1 wherein said treatment period is reduced compared to treatment with only isoniazid or isotopically labeled isoniazid.

10. The method according to claim 1 wherein said tuberculosis is drug resistant or multiple drug resistant tuberculosis.

11. The method according to claim 1 wherein said tuberculosis is isoniazid sensitive tuberculosis.

12. A method of improving the anti-tuberculosis activity of an isotopically labeled isoniazid compound in a patient or subject, the method comprising administering said isoniazid to a patient or subject and exposing said patient or subject to a magnetic field, wherein the magnetic field ranges from 10 to 1,000 Gauss.

13. A method of treating a subject suffering from, or at risk of developing, a *Mycobacterium* infection, the method comprising:
    (a) administering to the subject a therapeutically-effective amount of isotopically labeled isoniazid and/or ethionamide, or a pharmaceutically acceptable salt thereof; and
    (b) exposing the subject to a magnetic field of from 10-1,000 Gauss.

14. The method of treatment of claim 13, wherein the exposure of the subject to the magnetic field is concurrent with the administration of the therapeutically-effective amount of isotopically labeled isoniazid and/or ethionamide, or a pharmaceutically acceptable salt thereof.

15. The method of treatment of claim 13, wherein the magnetic field ranges from 50-250 Gauss.

16. The method of treatment of claim 13, wherein the subject suffers from tuberculosis.

17. The method of treatment of claim 13, wherein the isotopically labeled isoniazid is an isoniazid compound whose acyl group contains $^{13}$C and $^{17}$O.

18. The method of treatment of claim 13, wherein the isotopically labeled ethionamide is an ethionamide whose thioamide contains $^{13}$C and $^{33}$S.

19. The method of treatment of claim 18, wherein the subject suffers from tuberculosis and wherein the magnetic field ranges from 50-250 Gauss.

20. The method of treatment of claim 13, wherein:
    (a) the subject suffers from tuberculosis;
    (b) the isotopically labeled isoniazid is an isoniazid compound whose acyl group contains $^{13}$C and $^{17}$O and the isotopically labeled ethionamide is an ethionamide compound whose thioamide contains $^{13}$C and $^{33}$S; and
    (c) the magnetic field ranges from 50-250 Gauss.

21. The method of treatment of claim 13, wherein the subject suffers from tuberculosis and is administered one or more additional anti-tuberculosis agents.

22. The method of claim 20, wherein the isotopically labeled isoniazid is adisoniazid compound whose acyl group contains $^{13}$C and $^{17}$O and the isotopically labeled ethionamide is an ethionamide compound whose thioamide contains $^{13}$C and $^{33}$S.

23. The method of claim 22, wherein the magnetic field ranges from 50-250 Gauss.

24. The method of treatment of claim 13, wherein:
    (a) the subject suffers from tuberculosis and is administered one or more additional anti-tuberculosis agents concurrently with the isotopically labeled isoniazid and/or ethionamide, or a pharmaceutically acceptable salt thereof;
    (b) the subject is exposed to the magnetic field within twenty-four hours-of the administration of the isotopically labeled isoniazid and/or ethionamide, or salt thereof.

25. The method of claim 24, wherein:
    (a) the isotopically labeled isoniazid is an isoniazid compound whose acyl group contains $^{13}$C and/or $^{17}$O and the isotopically labeled ethionamide is an ethionamide compound whose thioamide contains $^{13}$C and/or $^{33}$S; and
    (b) the magnetic field ranges from 50-250 Gauss.

* * * * *